United States Patent [19]
Rock

[11] Patent Number: 5,348,878
[45] Date of Patent: Sep. 20, 1994

[54] CLASS I MHC-RESTRICTED T-T HYBRIDOMAS, AND A CD8-TRANSFECTED BW5147, FUSION PARTNER THEREFOR

[75] Inventor: Kenneth L. Rock, Chestnut Hill, Mass.

[73] Assignee: Dana-Farber Cancer Institute, Boston, Mass.

[21] Appl. No.: 814,069

[22] Filed: Dec. 24, 1991

Related U.S. Application Data

[63] Continuation-in-part of Ser. No. 521,838, May 10, 1990, abandoned.

[51] Int. Cl.$^5$ .............................................. C12N 5/16
[52] U.S. Cl. .............................. 435/240.26; 435/7.24; 435/29; 435/69.1; 435/172.2
[58] Field of Search ...................... 424/93 B; 435/7.24, 435/172.3, 172.2, 240.2, 240.26

[56] References Cited

PUBLICATIONS

Kanagawa, O., et al. (1989) J. Exp. Med. 170: 901–912.
Ratnofsky, S. E., et al. (1987) id,. 166: 1747–57.
Gu, J. J., et al. (1992) Immunogenetics 36: 283–93.
Kanagawa, O., et al. (1990) Intl. Immunol. 2: 957–64.
Weiner, D. B., et al. (1986) Cell. Immunol. 100: 197–209.
Dembic', Z. et al. (1987) Nature 326: 510–11.
Dembic', Z., et al. (1986) Nature 320: 232–38.
Haas, et al. (1985) Eur. J. Immunol. 15: 755–60.
Moore, et al. (1988) Cell 54: 777–85.
Burgert et al, "Reactivity of VB17a+ CD8+ T Cell Hybrids," *J. Exp. Med.*, 170: 1887–1904 (Dec., 1989).
Whitaker et al, "CT Hybridomas: Tumor Cells Capable of Lysing Virally Infected Target Cells," *Journal of Immunology*, vol. 129, No. 2, (1982).
Kaufman et al, "Cytotoxic T lymphocyte hybridomas that mediate specific tumor-cell lysis in vitro," *Proc. Natl. Acad. Sci., U.S.A.*, vol. 78, No. 4, 2502–2506 (1981).
Endres et al, "An IL-2 Secreting T Cell Hybridoma That Responds To A Self Class I Histocompatibility Antigen In The H-2D Region," *Journal of Immunology*, vol. 131, No. 4, pp. 1656–1662 (1983).
Gabert et al, "Reconstitution of MHC Class I Specificity by Transfer of the T Cell Receptor and Lyt-2 Genes," *Cell*, vol. 50, pp. 545–554 (1987).
Carbone et al, "Remethylation At Sites 5' Of The Murine Lyt-2 Gene In Association With Shutdown of Lyt-2 Expression," *Journal of Immunology*, 141: 1369–1375, (1988).
Hagiwara et al, "The AKR Thymoma BW5147 Is Able To Produce Lymphokines When Stimulated With Calcium Ionophore and Phorbol Ester," *Journal of Immunology*, vol. 140, No. 5, pp. 1561–1565 (1988).
Mossmann and Coffman, "TH1 and TH2 Cells: Different Patterns of Lymphokine Secretion Lead to Differ- (List continued on next page.)

Primary Examiner—Robert J. Hill, Jr.
Assistant Examiner—David L. Fitzgerald
Attorney, Agent, or Firm—Julia D. Hart

[57] ABSTRACT

The present invention provides class I MHC-restricted T-T hybridomas, a novel T-T fusion partner therefor and an assay system that allows for the generation and detection of functional, class I MHC restricted T-T hybridomas. The fusion partner comprises a murine BW5147 cell line that has been transfected with a CD8 gene and stably expresses the CD8 gene product. The BW5147 transfectants are used to generate functional, class I MHC restricted T-T hybridomas which are permissive for lymphokine production. Functional class I MHC-restricted T-T hybridomas exhibiting the capability of producing lymphokines are prepared by fusing BW5147 cells expressing CD8 with T lymphocytes activated in a mixed leukocyte reaction (alloreactive T cells) or stimulated with antigen (antigen-stimulated T lymphocytes) and screening the resulting hybrids for the ability to produce lymphokines in response to appropriate antigenic stimulation. Responsiveness of these clones to alloantigen or to antigen-MHC I complexes can be tested by measuring their production of lymphokines, which provides a sensitive and quantitative assay system.

14 Claims, 8 Drawing Sheets

PUBLICATIONS ence Functional Properties," *Ann. Rev. Immunol.,* 7:145–73 (1989).

MacDonald et al, "Clonal Heterogeneity in the Functional Requirement for Lyt-2/3 Molecules on Cytolytic T Lymphocytes (CTL) . . .", *Immunological Rev.,* vol. 68 (1982).

Silva et al, "RatXMourse T-Cell Hybrids with Inducible Specific Cytolytic Activity," Immunological Rev., vol. 76, 105–129 (1983).

Kappler et al, "Antigen-Inducible, H-2-Restricted, Interleuken-2-Producing T Cell Hybridomas," *J. Exp. Med.,* vol. 153, 1198–1214 (1981).

Rock and Benacerraf, "MHC-Restricted T Cell Activation: Analysis With T Cell Hybridomas," *Immunological Rev.,* vol. 76, pp. 29–57 (1983).

Rock and Benacerraf, "Inhibition of Antigen-Specific T Lymphocyte Activation By Structurally Related Ir Gene-Controlled Polymers," *J. Exp. Med.,* vol. 157, pp. 1618–1634 (1983).

Bierer et al, "The Biological Roles of CD2, CD4 and CD8 in T Cell Activation," *Ann. Rev. Immunol.,* 7: 579–599 (1989).

Rock, K., "Functional T-Cell Hybridomas", *Hybridoma Technology in BioScience and Medicine,* Timothy A. Springer, ed., Plenum Press, pp. 527–544 (1985).

CLASS I MHC-RESTRICTED T-T HYBRIDOMAS, AND A CD8-TRANSFECTED BW5147, FUSION PARTNER THEREFOR

This invention was made with Government support under the Grant A1-RO1-20248 from the National Institutes of Health. The United States of America has certain rights to this invention.

CROSS REFERENCE TO RELATED APPLICATION

This application is a continuation-in-part application of prior application U.S. Ser. No. 07/521,838, filed on May 10, 1990, now abandoned.

FIELD OF THE INVENTION

The present invention provides a novel murine fusion partner, class I MHC-restricted T-T hybridomas prepared with the novel fusion partner and an assay system that allows for the generation and detection of the functional class I MHC restricted T-T hybridomas.

BACKGROUND OF THE INVENTION

T lymphocytes have long been known to play a principal role in the regulation of the immune response. The T lymphocytes can be roughly divided into three compartments; the T inducer (helper) cells, cytotoxic T lymphocytes (CTL) and suppressor T cells. The activation of T lymphocytes occurs upon interaction with cells bearing appropriate antigen in the context of major histocompatibility complex (MHC) proteins. Specificity of the T cell response is conferred by the polymorphic, antigen-specific T cell receptor (TCR). In addition to the antigen specific TCR, a number of other cell surface proteins regulate T cell activation and impart sensitivity and plasticity to the immune response. These include the surface antigens CD2, CD4 CD8 and lymphocyte function associated antigen. Such surface antigens are non-polymorphic molecules that not only increase the avidity with which a T cell interacts with its antigen presenting cell (APC) or target cell but also may play a role in signal transduction. The CD4 and CD8 molecules are expressed on mutually exclusive populations of mature T cells that bear TCRs specific for antigen in association with MHC class II and MHC class I proteins, respectively. These molecules appear to enhance the avidity with which a T cell binds with its antigen bearing or target cell and may also promote the interaction of the TCR with its appropriate antigen. Bierer et al, "The Biologic Roles of CD2, CD4 and CD8 in T-cell Activation," *Ann. Rev. Immunol.*, 7:579-99 (1989).

The phenomenology of MHC-restricted T lymphocyte interactions has previously been well documented. Cells of the T helper/inducer subset will generally recognize antigen only in association with class II major histocompatibility (MHC) gene products. Recognition occurs on the surface of antigen presenting cells and accounts for the MHC genetic restriction of antigen recognition. Cytotoxic T lymphocytes (CTL), which are well known effector cells in transplantation immunity, viral infection and certain anti-tumor responses, generally recognize antigen in association with class I MHC gene products. While the rules governing the activation of MHC-restricted T cells, and particularly of class II MHC-restricted T cells have been well described, the underlying mechanisms are still being defined.

Most of the understanding in the art of T lymphocyte biology has come from in vivo studies and in vitro experiments using heterogeneous T cell populations. Such methodologies have certain inherent limitations, including low frequency of specific T lymphocytes and the potential for multicellular complex interactions. More recently, a better understanding of T cell activation and of the factors involved has allowed for the isolation and propagation of T cell lines and clones of defined specificity. Two basic strategies have been devised. One approach is to clonally expand and propagate normal immune T lymphocytes through the repetitive stimulation with the appropriate antigen, with or without the presence of growth factors. The second approach parallels the approach that has been utilized to produce monoclonal antibodies from B cell hybridomas prepared by cell hybridization of antibody-producing B cells and myeloma cells, and involves the immortalization of T lymphocytes through somatic cell hybridization with T cell lymphomas.

The latter methodology has been used extensively for the production of antigen-specific, class II MHC-restricted, T-T hybridomas, which have several advantageous properties. See, e.g. Kappler, et al, "Antigen inducible, H-2 restricted, interleukin-2 producing T cell hybridomas. Lack of independent antigen and H-2 recognition", *J. Exp. Mede*, 153:1198; (1981), Rock, K. L., "Functional T-cell Hybridomas, in Hybridoma Technology in the Biosciences and Medicine.," Ed. T. A. Springer, Plenum Press, N. Y. (1985). These hybridomas have essentially limitless growth potential and grow readily under standard culture conditions. Furthermore, the immunological activity of these hybridomas is not subject to cyclic fluctuations, as is seen with restimulated normal clones. The T-inducer hybridomas produce lymphokines in response to T cell receptor (TCR) stimulation, which provides a sensitive and quantitative assay to measure cellular activation. Consequently, the class II MHC-restricted T-T hybridomas have proven to be particularly useful in the analysis of the structure and function of surface receptors, cell-cell interactions and T cell activation involving T helper cells. See, for example, Rock, K. L., "Functional T-cell Hybridoma", in *Hybridoma Technology in the Biosciences and Medicine*, Ed. T. A. Springer, Plenum Press, N. Y. (1985); Marrack, P. and J. Kappler. "The antigen-specific, major histocompatibility complex-restricted receptor on T cells." *Adv. Immunol.* 38:1 (1986), Bierer, B. E., et al, "The biologic roles of CD2, CD4, and CD8 in T cell activation." *Ann. Rev. Immunol.* 7: 579 (1989). Moreover, since the T-inducer hybrids do not generally require costimulatory signals, it has been possible to stimulate them with fixed or disrupted antigen presenting cells as well as model membrane systems. Shimonkevitz, R. J. et al, "Antigert recognition by H-2 restricted T cells. Cell-free antigen processing," *J. Exp. Med.* 158:303, (1983), Watts, T. H. et al, "Antigen presentation by supported planar membranes containing affinity purified $IA^d$.) *Proc. Natl. Acad. Sci. USA* 81:1883 (1984). Therefore, antigen-specific class II MHC restricted T-T hybridomas have provided a powerful and useful tool in analyzing the events in antigen presentation by providing an assay to follow the appearance of antigen-MHC class II molecule complexes.

In contrast to the above results, there has been only limited success in generating antigen-specific class I MHC restricted T cell hybridomas, particularly with the most commonly used murine fusion partner, the BW5147 thymic lymphoma. Heretofore, such fusions with BW5147 have generally been unproductive. The reason why such hybrids have not been easily obtained from fusions with BW5147 is not known.

Despite the foregoing, there have been isolated reports of successful generation of class I MHC-restricted hybridomas with BW5147. Whitaker et al, for example, have described the preparation of H-2 restricted, reovirus-specific cytotoxic T cell hybrids using BW5147 as a fusion partner. "CT hybridomas: Tumor Cells Capable of Lysing Virally Infected Target Cells," *Journal of Immunology*, vol. 129, no. 2 pp. 900–903. These hybrids, however, require a mitogenic lectin for stimulation and do not respond well to antigen and appropriate antigen presenting cells alone. Other examples of class I MHC-restricted hybridomas generated with BW5147 cells have previously been reported by Kaufmann, Y. G. et al, "Cytotoxic T. Lymphocyte T cell hybridomas that mediate specific tumor-cell lysis in vitro.", *Proc. Natl. Acad. Sci. USA*, 78:2502, (1981), and by Endres, R. P. et al, "An IL-2 secreting T cell hybridoma that responds to a self class I histocompatibility antigen in the H-2D region.", *J. Immunol.* 131:1656 (1983). However, such hybrids are identified at low frequency and may represent "high affinity" T cells that are not CD8 dependent. See, MacDonald et al, "Clonal Heterogeneity in the functional requirement for Lyt-2/3 molecules on cytolytic T Lymphocytes (CTL): Possible implications for the affinity of CTL antigen receptors.", *Immunol. Rev.* 68:89 (1982). Furthermore, the successful isolation of such hybridomas has been limited to those that are MHC reactive (e.g. allo- or auto-reactive) and has not been described for antigen-specific, MHC-restricted cells.

Other fusion partners have been employed to generate class I MHC-restricted T-T hybrids, but such cells have not achieved widespread usage. Accordingly, there exists a need for an immortalized fusion partner which will allow for the successful generation and detection of class I, MHC-restricted T-T hybridomas, including those that are CD8 dependent.

In those instances where somatic hybridization technology has been used to establish functional class I MHC-restricted T cell hybrids, screening of the clones for responsiveness to class I MHC alloantigens or to antigen plus class I MHC proteins has typically been conducted using a conventional chromium release assay. This assay is routinely employed in the study of cytotoxic T cells and involves incubation of serial dilutions of cytolytic effector cell populations in the presence of a constant number of $^{51}Cr$ labeled target cells at low effector to target ratios. At these low ratios, each effector cell is saturated with targets and kills at maximum efficiency. After a prescribed period of time, the radioactivity released into the supernatants is measured and the percent specific cytotoxicity can be calculated.

Since what is being measured in the chromium release assay is the cytolytic capability of the effector cells, this assay necessarily requires the use of intact target cells. This requirement constrains the experimental manipulation of target cells, for example with drugs or chemical reagents. Moreover, intact cells have a tendency to retain the isotope and hence, measurement of the isotope release does not completely reflect the strength of the CTL response. Another disadvantage of the chromium release assay is that it is labor intensive and presents the potential of health and safety risks. In view of all of the foregoing, an alternative assay for screening for the cytotoxic fusion product and for studying antigen presentation in association with class I MHC-restricted molecules is indicated.

Although it has been observed that many cytotoxic T lymphocytes have the capacity to produce lymphokines in response to antigen, they generally produce lower levels of lymphokines such as IL-2. Accordingly, this capability has not been employed in the study of the events of class I MHC-restricted antigen presentation and cell-cell interaction.

Accordingly, it is an object of the present invention to provide a novel BW5147 fusion partner for the generation and detection of stable, functional, class I MHC-restricted T-T hybridomas.

Another object of the present invention is to provide a BW5147 fusion partner which is permissive for lymphokine production in class I MHC-restricted T-T hybridomas.

A still further object of the present invention is to generate lymphokine producing, class I MHC-restricted T-T hybridomas using BW5147 as a fusion partner.

Yet another object of the present invention is to provide a quantitative and sensitive assay for the generation and detection of lymphokine-producing, class I MHC-restricted hybrids.

These as well as other objects and advantages are accomplished by the present invention, the nature and scope of which will become apparent from the following specification.

SUMMARY OF THE INVENTION

The present invention provides class I MHC-restricted T-T hybridomas, a novel T-T hybrid fusion partner therefor and assay system that allows for the generation and detection of the functional, class I MHC-restricted T-T hybridomas. The fusion partner comprises a murine BW5147 cell line that has been transfected with a CD8 gene and stably expresses the CD8 gene product. The BW5147 transfectants are used to generate functional, class I MHC-restricted T-T hybridomas which are permissive for lymphokine production. Functional class I MHC-restricted T-T hybridomas exhibiting the capability of producing lymphokines are prepared by fusing BW5147 cells expressing CD8 with T lymphocytes activated in a mixed leukocyte reaction (alloreactive T cells) or stimulated with antigen (antigen stimulated T lymphocytes) and screening the resulting hybrids for the ability to produce lymphokines in response to appropriate antigenic stimulation. Responsiveness of these clones to alloantigen or to antigen-MHC class I complexes can be tested quantitatively by measuring their production of lymphokines, which provides a sensitive and quantitative assay system.

The assay of the present invention involves obtaining a class I MHC-restricted T-T hybridoma capable of lymphokine production by fusing BW1547 T cells which express the CD8 molecule, and lack the enzyme hypoxanthine guanine phosphoribosyl transferase (HGPRT), with stimulated T lymphocyte cells, selecting the hybrids which grow in media containing hypoxanthine, aminopterin and thymidine (HAT), culturing the hybrids thus obtained with antigen and appropriate MHC class I target or antigen presenting cells (APC'S), removing the supernatant from the cultures, assaying the supernatants thus obtained for the production of lymphokines and isolating T-T hybridomas that are class I MHC restricted.

BRIEF DESCRIPTION OF THE DRAWINGS

(FIG. 3A): A C57BL/6 anti-OVA $+k^b$ X BW. CD8.7, T-T hybridoma (RF33.70); (FIG. 3 C): A C57BL/6 anti-class I, H-$2^d$-alloreactive X BW5147 T-T hybridoma.

DETAILED DESCRIPTION OF INVENTION

Figure 1A:
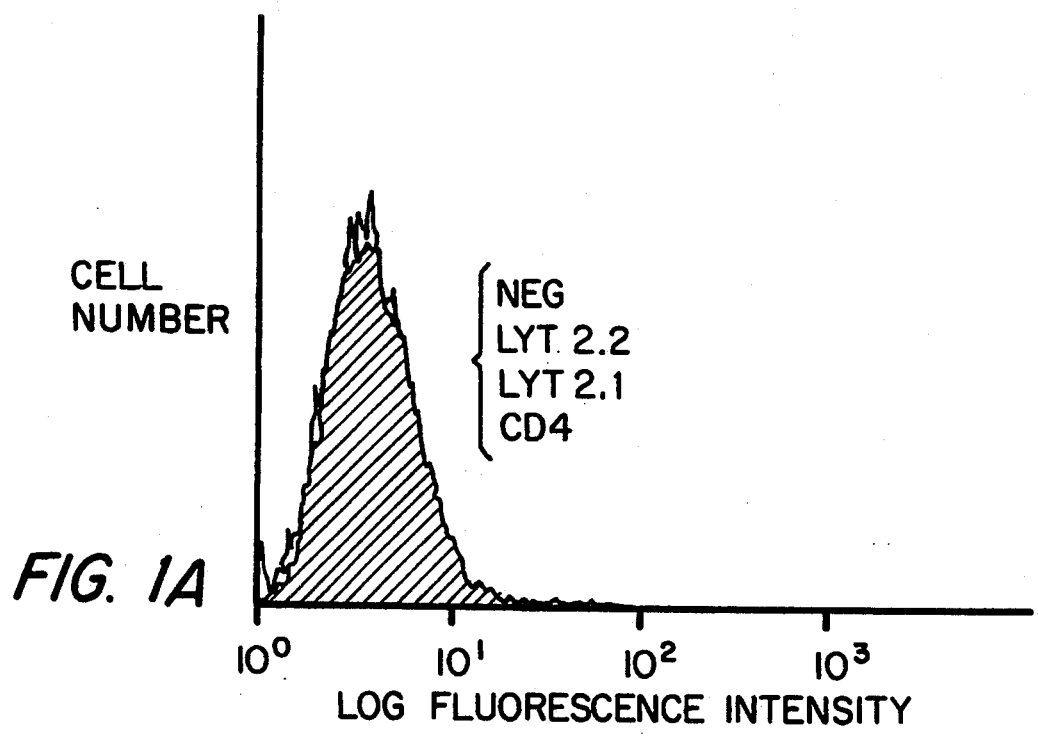
FIGS. 1A and B are fluorescent histograms obtained from the flow cytometric analysis of BW5147 and a BW5147-CD8 transfectant, respectively. BW5147 cells (FIG. 1 A) or BW.CD8.7 (a hygromycin resistant clone of BW5147 transfected with pSV2hph/CD8) (FIG. 1 B) were prepared for indirect immunofluorescence staining with MKD6 (NEG), HO.2.2ADH4 (Lyt-2.2), 116.13 (Lyt-2.1) or GK1.5 (CD4) monoclonal antibodies. Fluorescence was analyzed on a FACSCAN flow cytometer and data are displayed as cell number on the ordinate versus log relative fluorescence intensity on the abscissa. The background (NEG) curve is cross-hatched; other curves are unshaded.

The present invention is directed to class I MHC-restricted T-T hybridomas, a novel T-T hybrid murine fusion partner therefor, derived from the BW5147 cell line, and to an assay system which allows for the generation and detection of lymphokine-producing, class I MHC-restricted T-T hybridomas. The rationale for this approach was based upon several observations. First, many cytotoxic T lymphocytes appear to have the ability to produce lymphokines. See, Mussman and Coffman, "TH1 and TH2 Cells, Different Patterns of Lymphokine Secretion Lead to Different Functional Properties," *Ann. Rev. Immunol,* 7:145–73 (1989). For example, mouse T cell clones of the Lyt-2+, cytotoxic phenotype express a pattern of lymphokine elaboration that corresponds to the TH1 (T helper 1) pattern, showing good levels of interferon (INF) gamma, TY5, and moderate amounts of GM-CSF, interleukin (IL) 3, lymphotoxin, (LT), tumor necrosis factor and IL-2. Second, BW5147 is permissive for lymphokine production in hybridomas, as evidenced by the class II MHC-restricted T-helper hybrids. Therefore, it was hypothesized that CTL-BW5147 hybrids might retain the ability to produce lymphokines. In addition, the activation signals transduced by class I and class II T cell receptors are probably identical. Accordingly, when class I MHC-restricted T cell receptors are introduced into class II MHC-restricted T-T hybridomas, they are capable of stimulating lymphokine production. See Gabert et al, "Reconstitution of MHC class I specificity by transfer of the T cell receptor and Lyt-2 genes," *Cell,* 50: 545–554 (1987). Finally, BW5147 alone has the endogenous capacity to produce lymphokines after stimulation with calcium ions and phorbol esters. Hagiwara, H. T. et al, "The AKR thymoma BW5147 is able to produce lymphokines when stimulated with Ca ionophore and phorbol ester," *J. Immunol.* 140:1561 (1988).

In order for this approach to be successful, it is necessary that antigen in association with class I MHC molecules be appropriately recognized by the class I MHC-restricted T-T hybrids. One of the limitations of using BW5147 is that it does not express the CD8 molecule, and it does not generally allow for the expression of CD8 molecules even upon hybridization with CD8+T lymphocytes. In hybridomas that do express surface CD8, expression is transient and greatly diminished in terms of the number of CD8 molecules per cell. See, Carbone et al, "Remethylation At Sites 5' of The Murine Lyt-2 Gene in Association With Shutdown Of Lyt-2 Expression," *Journal of Immunol.*, vol. 141, No. 4, pp. 1369–1375 (August 1988). Since many of the class I MHC-restricted T lymphocytes and particularly the class I restricted cytotoxic T lymphocytes are dependent on the presence of CD8, the failure of BW5147 to express the CD8 molecule could impede the detection of class I MHC-I restricted hybrids. Accordingly, it is an object of the present invention to provide a BW5147 cell line expressing the CD8 molecule.

The CD8 molecule, alternatively denoted Lyt-2,3 in the mouse and T8 in humans, is a T lymphocyte surface molecule that is believed to enhance the overall avidity of class I MHC-restricted T lymphocytes for their target cells. The murine CD8 molecule is a heterodimer or homodimer comprising the products of the genes encoding for the Lyt-2 and Lyt-3 subunits. The genes encoding the Lyt-2 and Lyt-3 subunits have previously been characterized by a number of investigators. Recent evidence has suggested that, besides the TCR alpha beta heterodimer, the Lyt-2 polypeptide is the only subset specific accessory molecule required for the functional recognition of MHC class I antigen. Gabert et al, "Reconstitution of MHC class I Specificity by Transfer of the T Cell Receptor and Lyt-2 Genes," cell, vol. 50, pp. 545–554 (August 14, 1987). The Lyt-2 gene exists in two different allelic forms, Lyt-2.1, Lyt-2.2, although there are presently no known functional differences between these allelic forms.

On the peripheral T cells, the human CD8 molecule (T8) is composed of homomultimers of a single 34 kd subunit, which is the homologue of murine Lyt-2. Human thymocytes express homodimers of the 34 kd subunit, as well as heteromultimers of the 34 kd subunit with CDi(T6). The gene encoding the human T8 gene has previously been cloned by a number of investigators and reported in the published literature. See, for example, Kavathas et al., "Isolation of the gene encoding the human T-lymphocyte differentiation antigen Leu-2 (TS) by gene transfer and cDNA subtraction. *Proc. Natl. Acad. Sci. USA* 81, 7688, (1984); Littman et al., "The isolation and sequence of the gene encoding TS: a molecule defining functional classes of T lymphocytes." *Cell* 40:237 (1985).

In one embodiment, the present invention provides novel BW5147 transfectants that constitutively express the CD8 molecule. The gene encoding CD8 can be of murine or human origin.

The BW5147 cell line is an azaquanine resistant, immature, AKR thymic lymphoma which is frequently used as a fusion partner in the preparation of class II MHC-restricted hybridomas, as previously described. More specifically, it is an immature CD4− CD8− AKR thymic lymphoma that lacks the hypoxanthine-guanine phosphoribosyl transferase (HGRT) enzyme. The BW5147 cell line is well known and can be readily obtained and cultured by those skilled in the art.

The novel fusion partners of the present invention are obtained by transfecting the BW5147 cell line with a clone of the CD8 gene, encoding for at least the Lyt-2 subunit of murine CD8, or for the T8 subunit of human CDS. A gene encoding for either the murine Lyt-2.1 or Lyt-2.2 allelic form can be used in the transfection and may additionally include the gene for Lyt-3. Clones of the Lyt-2 gene are known and available to persons skilled in the art. One source of the Lyt-2 gene is the pCA208 plasmid, containing a 4.5 Kb DNA insert encoding the Lyt-2.2 allele of murine CDS, which was originally cloned by Parnes See, Zamoyska, R. A. et al, "Two Lyt-2 polypeptides arise from a single gene by alternative splicing patterns of mRNA." *Cell* 43: 153, (1985). Other investigators have used the Lyt-2.2 containing pCA208 plasmid for the transfection of class II, MHC-restricted hybridomas. See, Gabert et al, previously cited. DNA coding for the Lyt-2 gene can alternatively be obtained from other sources. For example, Zamoyska described the lambda cLy2.10 clone as being a source of a cDNA encoding the Lyt-2 polypeptide. Zamoyska et al., "Two Lyt-2 polypeptides arise from a single gene by alternative splicing patterns of mR/qA". *Cell* 43:153 (1985). Tagawa described the pLyt-2 alpha' vector as being a source of a cDNA encoding the Lyt-2 polypeptide. Tagawa et al., "Formal proof that different-size Lyt-2 polypeptides arise from differential splicing and post-transcriptional regulation." *Proc., Natl. Acad. Sci. USA,* 83:3422 (1986). In addition, mouse or human CD8 cDNAs or genomic clones can be readily isolated from cDNA or genomic libraries by hybridization with oligonucleotide probes synthesized based on the published gene sequences by standard techniques.

Transfection of BW5147 with the CD8 gene can be accomplished by any of the conventional methods for transfecting mammalian cells, including spheroplast fusion, calcium phosphate or DEAE dextran mediated transfection, liposomes and electroporation. In a preferred embodiment, plasmid transformed bacteria are converted into spheroplasts in accordance with conventional techniques, which are in turn used to transfect the BW5147 cells. A more detailed description of this method of transfection is provided by way of example below. Alternatively, plasmids carrying the CD8 gene can be used in a liposome-plasmid mixture, which is then added to the culture of BW5147 cells.

In the case of plasmid-mediated transfection, the CD8-containing plasmid employed in the transfection procedure preferably includes a dominant selectable marker that can subsequently be used to detect transfected cells. Resistance to antibiotics is a well known and frequently used selectable marker for transfected cells. For example, the CD8 insert coding for Lyt-2.2 can be excised from the pCA208 plasmid with the restriction enzyme Sal I using known techniques and subcloned into the Sal I site of the pSV2hph vector, which contains the hygromycin B phosphotransferase gene under the control of an SV40 promoter and enhancer. This latter gene provides a dominant selectable marker (i.e. resistance to hygromycin B) that does not interfere with subsequent selection of transfected cells in HAT media. The pCA208 vector, from which the CD8 gene is excised, has a dominant selectable marker (the GPT gene), however this marker interferes with HAT selection. Other known plasmids can be used in the transfection of BW5147 with the CD8 gene, including those that contain a dominant selectable marker and similarly do not interfere with subsequent selection of transfected cells in HAT media.

Transfected cells can be selectively obtained by culturing the resulting cells with a conventional selective media which permits proliferation of the desired transfected cells only, but inhibits proliferation of the non-transfected cells. For example, a medium containing hygromycin B can be used to select for the transformants transfected with the Sv2hph vector, which includes the gene coding for resistance to hygromycin B. A useful example of hygromycin B containing media is prepared by adding 1.3–2 mg/ml hygromycin B (Sigma, St. Louis, Mo.) to standard hybridoma culture media, e.g. RPMI 1640, 10% FCS. The cells are cultured in the selection media by the conventional limiting dilution method for a period of time, usually several days to several weeks, sufficient to allow the death of the non-transfected cells.

Clones obtained following the selection of transformants are then analyzed for CD8 expression by known methods. For example, clones exhibiting CD8 expression may be identified by indirect immunofluorescence and flow cytometry using known antibodies to the CD8 phenotype. Cells are prepared for indirect immunofluorescence, as previously described, for example, by Zamoyska, et al, "Two Lyt-2 polypeptides arise from a single gene by alternative splicing patterns of mRNA," *Cell* 43: 153 (1985), using Anti-Lyt-2 monoclonal antibody culture supernatant followed by fluorescein isothiocyanate rabbit anti-mouse Ig. Examples of Anti-Lyt-2.1 monoclonal antibodies which can be used in the identification of Lyt-2.1 expressing transfectants include 116-13.1 (mouse IgG, specific for Lyt-2.1); Examples of Anti Lyt-2.2 monoclonal antibodies include 2.43 (rat IgG specific for Lyt-2.2), H02-2ADH4 (anti-Lyt-2.2) and 41-3.48 (anti-Lyt-2.2). Antibodies to human T8 are similarly known, and include, for example, OKT8 (anti-CDS).

In accordance with the present invention, BW5147.CD8 transfectants are obtained with good frequency. Such transfectants are generated at a frequency of about 1 transfectant in about $10^4$ to $10^6$ cells. Like BW5147, the BW5147 transfectants, sometimes hereinafter designated BW.CDS, are azaguanine resistant and die in a medium (HAT) containing hypoxanthine, aminopterin and thymidine. The BW.CD8 transfectants can be cultured for at least three months with stable expression of CD8 and can be preserved by freezing. It is expected that stable expression can be maintained for longer periods and that expression can be selected for by culture in the appropriate antibiotic.

The BW5147 transfectants expressing CD8 can be cultured in various nutrient media which are substantially synthetic but which can contain a natural ingredient, such as serum. An example of a preferred nutrient medium is RPMI 1640 medium (Irvine Scientific, Santa Ana, CA), supplemented as previously described by Rock, "The role of Ia molecules in the activation of T lymphocytes. I. The activation of an IL-1 dependent, IL-2 producing T cell hybridoma by Con A requires an interaction, which is not H-2 restricted with an Ia bearing accessory cell," *J. Immunol.* 129:1360 (1982). The BW5147 fusion partner of this invention grown on such media can be readily adapted to proliferate on various media which are generally used in the art, such as FCS-containing minimum essential Eagle media (MEM). To maintain the fusion partner cell line of this invention, the media should, although it need not, contain hygromycin. The cells can De cultured in these media under conditions which are generally employed for the culture of BW5147 cells.

A representative example of the BW5147 transfectants expressing the murine CD8 gene (Lyt-2.2) and obtained in accordance with the present invention, BWCDS.7, was deposited with the American Type Culture Collection (ATCC), 12301 Parklawn Drive, Rockville, Md., 20852 on Mar. 14, 1990 and has been assigned the ATCC accession number CRL 10387.

In another embodiment, the present invention provides lymphokine-producing functional class I MHC-restricted hybridomas comprising the fusion product of (i) the murine T cell line BW1547, which has been transfected to express the CD8 molecule and (ii) class I MHC-restricted T lymphocytes, wherein the hybridoma is capable of lymphokine production upon stimulation with allogeneic class I molecules or with antigen in association with class I MHC molecules on the surface of antigen presenting cells.

Functional, lymphokine-producing class I MHC-restricted T-T hybridomas have been prepared in accordance with the present invention with T lymphocytes (alloreactive T lymphocytes) which respond to allogeneic class I MHC molecules on a cell surface, and with T lymphocytes whose specificity is for antigen in association with self class I molecules (antigen specific T lymphocytes). As used herein, "allogeneic" class I molecules denote class I molecules on lymphocytes that are of the same species, but antigenically distinct from, the class I molecules on the surface of the responding T lymphocytes. The specificity for the antigen-specific T lymphocytes is, for example, for viral or hapten antigens in association with syngeneic, or self class I molecules. In accordance with the present invention, hybrids can be obtained by the fusion of BW5147 transfectants expressing murine or human CD8, with murine or human T lymphocytes cells, respectively.

The hybrids of the present invention are useful in the analysis of the properties of the individual T cells, as well as the underlying cellular and molecular events important in their activation. For example, the hybrid clones are well suited for analyzing individual T cell specificities. The hybrids can also be used to explore the molecular events underlying T cell activation. For example, the class I restricted hybrids can be used to identify the determinants on antigens that are critical to cytotoxic T lymphocyte activation. Such hybrids are also useful in dissecting the role of class I molecules in antigen presentation and for analyzing the processing of antigen for presentation. Alloreactive hybrids can be used to probe class I molecule determinants, for detection of class I molecule alterations. In addition, the production of lymphokines by the T-T hybrids generated with the transfected BW5147 expressing CD8 can be measured with a sensitive and quantitative assay. These features provide advantages over the use of cytotoxic T lymphocytes with cytolytic assays, since the $^{51}$Cr release assay requires intact APCs which readily take up and retain the isotope. In addition, the assay of the present invention allows for the manipulation of target cells, as by fixation or treatment with drugs, which provides a significant advantage over the prior art.

The T lymphocytes which can be used for fusion with the BW.CD8 transfectants are not particularly limited. Examples of useful T cells include those obtained from the peripheral blood, bone marrow, lymph nodes, tonsils and thymus. Such T lymphocytes can be isolated and or purified by various separating methods which are known, such as conventional physical methods, chemical methods and the adherence method to surface membranes and can be used for fusion in accordance with the present invention.

Antigen-specific T lymphocytes are preferably obtained by immunizing the host with live or attenuated infection (for vital specific cells) or subcutaneous injection of haptenating compounds or haptens coupled to cell surfaces, isolating the lymphocytes from the host and enriching for antigen-specific T lymphocytes prior to fusion. Alternatively, a naive population of cells can be removed and primed for CTL response in vitro. Several strategies known in the art have been employed to enrich antigen-specific T lymphocytes. One strategy is to supply the requisite signals for continued clonal expansion in vitro. Under these conditions, specific cells increase in number and the irrelevant cells are diluted or die out. After a single restimulation with antigen, frequencies of greater than 1:100 can be achieved. With preferential fusion of activated T cells, specific hybrids can be as frequent as one in five. Cytotoxic T lymphocytes will require antigen/MHC stimulation as well as helper factors. The latter will be generated in cultures from T inducer cell stimulation. If these cells have been depleted, they must be reconstituted or a source of helper factor added. Supernatant from mitogen-stimulated T cells (from which mitogen has been removed or inactivated) or from secondary mixed lymphocyte cultures are convenient sources of helper factors.

The T cells to be used in the fusion can also be alloreactive T lymphocytes, activated, for example, in vitro by mixed lymphocyte culture (MLR). The mixed lymphocyte reaction represents a reaction in which lymphocytes from a first strain (the responder strain) are mixed with lymphocytes from a second strain (the stimulator strain), the latter bearing allogeneic class I molecules, having been irradiated or treated with mitomycin C so that they can not divide. Under this one way mixed lymphocyte culture condition, the second strain cells serve only as stimulator cells, as they are unable to proliferate. After five to seven days of incubation, the responder cells are tested for CTL activity against cells of the stimulator strain bearing allogeneic class I molecules.

Examples are given later in which the production of antigen-specific class I MHC-restricted hybridomas and alloreactive class I hybridomas are described in detail.

The fusion reaction between the HGPRT deficient BW5147 CD8 transfectants and the somatic T lymphocytes is conducted in substantially the same manner as in the known method of cell fusion in the presence of a fusion promotor in a suitable medium. Viruses, such as the Sendai virus (HVJ) are usable as fusion promotors, but it is preferable to use polyethylene glycol (PEG) as the fusion promotor. Preferably, PEG having a molecular weight of about 1000 to 6000 is employed. It is suitable that the medium contain such PEG at a concentration of about 30 to about 60 W/V %. Different lots of PEG will significantly affect fusion frequencies. This must be determined empirically and optimal length of incubation in PEG may have to be adjusted. Pretested PEG can be obtained from the American Type Culture Collection, in Rockville, Md.

Useful culture medium for the fusions include MEM medium, Dulbecco's modified MEM medium, RPMI 1640 medium and other media which are useful for culturing cells. When desired, the medium may have incorporated therein an auxiliary agent for improving fusion efficiency.

The proportions of the BW.CD8 transfectant fusion partner and the murine T cells to be used for fusion are not particularly limited. Generally, the number of somatic T cells can be about 1–10 times the number of BW.CD8 parental cells. Preferably the ratio is about 4:1. The cells are preferably fused in the manner described by Rock, in "Functional T Cell Hybridomas" in Hybridoma Technology in the Biosciences and Medicine, Ed. T. A. Springer, Plenum Press, N.Y. (1985), the pertinent portions of which are incorporated by reference. An example of this method of fusion is provided in Example 2. Other variations of the PEG fusion reaction are known and can alternatively be employed.

Fused cells can be selectively obtained by culturing the resulting mixture with a conventional selective medium which permits the proliferation of the desired hybrid cells, but inhibits proliferation of the parental cells. (T lymphocytes are inherently incapable of proliferating in the selective medium). Typical of the medium used for hybrid selection purposes is HAT medium, a medium containing hypoxanthine, aminopterin and thymidine. The preparation of selective HAT media is well known in the art.

About 24 hours after the fusion process, the culture medium is replaced with HAT medium. The cells are then cultured in the presence of the HAT medium by the conventional limiting dilution method for a period of time, usually several days to several weeks, to allow death of the unfused cells. The cultures should preferably be fed with HAT medium, about 50–100 $\mu$l every five days. With BW.CDS, hybrids will usually appear in 7–21 days. When they achieve $\frac{1}{2}$–182's confluence, they can be transferred to 1–2 macrowells in HAT medium. Transfer of low density wells or over dilution will result in poor yields and should be avoided. Subsequently, the macrowells can be passaged at least two times in HT medium before changing to regular medium.

The hybridomas are screened for their ability to secrete lymphokines in response to antigenic stimulation with appropriate target cells or antigen and APC's and hybrids that are class I MHC-restricted are isolated. The cells can be screened as soon as sufficient numbers are grown, whether or not they are in PLAT. Class I MHC-restricted alloreactive hybrids can be detected based upon their ability to produce lymphokines in the presence of class I, but not class II MHC molecules. Antigenic stimulation of alloreactive class I MHC-restricted T-T hybridomas involves culturing the hybrids in the presence or absence of target cells bearing allogeneic class I MHC or class II molecules shared by the stimulator strain.

Antigenic stimulation of hybrids generated from antigen-specific T lymphocytes involves culturing the T-T hybrids in the presence of the antigen and antigen-presenting cells bearing syngeneic class I MHC molecules. Antigen presenting cells can be macrophages, T lymphocytes, or B lymphocytes bearing the appropriate class I MHC restriction pattern.

The proportions of antigen presenting or target cells to be utilized in the screening assays are not particularly limited. Generally, the T-T hybrids will be present in the microculture in a ratio of about 1–100 times the APC's or target cells and preferably in a ratio of about 2 to 1. The thus prepared microcultures are then incubated for a period of time of from about 18 to about 24 hours. The amount of lymphokine secreted by antigen-stimulated T-T hybrids is then measured with a quantitative bioassay, such as has previously been described for antigen-specific, I region-restricted (class II MHC-restricted) hybrids. See e.g., Kappler, J. W. et al, "Antigen inducible, H-2 restricted, interleukin-2 producing T cell hybridomas. Lack of independent antigen and H-2 recognition." *J. Exp. Med. 153:1198*, (1981). Rock, K. L. et al, "Inhibition of antigen-specific T. lymphocyte activation by structurally related Ir gene-controlled polymers. Evidence of specific competition for accessory cell antigen presentation." *J Exp. MeG.* (1983).

A preferred bioassay involves screening the microculture supernatant for the production of interleukin-2 (IL-2). This assay involves the harvesting of culture supernatant, generally in an amount of about 100 $\mu$l and exposing the supernatant to 8,000 rads gamma irradiation or freezing and thawing. IL-2 content is measured by adding a fixed number of IL-2 dependent cells, usually from about $0.5 \times 10^4$ to about $10^4$ cells per 100 $\mu$l of culture supernatant and incubating for 20–26 hours with 1 $\mu$Ci of tritiated thymidine added over the last 4–6 hours.

Cultures are then harvested on glass filter strips with the aid of a semi-automated cell harvester and the incorporation of the label into DNA is determined by scintillation counting. Several modifications of this methodology are known and can alternatively be employed in accordance with the present invention.

A number of IL-2 dependent cells lines are known in the art. In accordance with a preferred embodiment of the present invention, either of the IL-2 dependent cells, CTLL, (Gillis et al, "T Cell Growth Factor: parameters of production and a quantitative microassay for activity", *J. Immunol.*, 120:2027 (1978)) or HT2, (Kappler et al, "Antigen-Inducible H-2 restricted, interleukin-2 producing T cell hybridomas. Lack of independent antigen and H-2 recognition," *J. Exp. Med*, 153:1198 (1981) are employed. Each of these two cell lines has an absolute requirement for IL-2 for viability and growth.

The hybridomas prepared in accordance with the present invention could alternatively be screened for the production of other lymphokines in response to the appropriate antigenic stimulation. For example, hybridomas can be screened for the production of interleukin-3 with IL-3 dependent cell lines or by ELISA assay. Interferon gamma can also be assayed by ELISA assay. See, for example, Cherwinski et al, "Further differences in lymphokine synthesis between TH1 and TH2 clones revealed by RNA hybridization, functional monospecific bioassays and monoclonal antibodies," *J. Exp. Med.*, 166:1229 (1987). GM-CSF can be assayed by ELISA assay. See Mossmann et al, supra.

One of the advantages of the assay of the present invention is that it does not require the use of intact, antigen presenting cells, as required with the standard chromium release assay currently employed in studies relating to the structure and function of class I MHC-restricted cytotoxic T lymphocytes. Fixed or otherwise inactive antigen presenting cells can be employed. The present assay system also has the obvious advantage of limiting the necessity for the use of the chromium release assay system, which is quite labor intensive and poses some health and safety risks as a result of the use of the radioactive chromium.

In accordance with the present invention, it has been found that many of the hybrid clones are capable of producing lymphokines, including IL-2, upon stimulation. The frequency of antigen-reactive hybridomas is dependent on the frequency of antigen-reactive T cells used in the fusion. Therefore, the frequency will vary in different fusions. For MLR activated T cells, the frequency of reactive cells is very high and in these fusions, a frequency of 1 in 5–10 class I reactive and 1 in 3–10 class II MHC reactive is obtained. This is as good as is achieved with standard BW5147 fusions for class II reactive cells which has not heretofore been achieved for class I hybrids.

The lymphokine-producing, class I MHC-restricted T-T hybridomas thus obtained can be proliferated in conventional medium using conventional techniques. The hybridomas grow vigorously in conventional serum-containing media and do not require special growth factors. These cells display a similar functional stability to that observed with class II MHC-restricted hybrids and are easily frozen and recovered with good viability and activity.

The present invention will be more clearly understood from the following specific examples.

EXAMPLE 1

Transfection of BW5147 with the CD8 gene (a) Plasmid preparation.

A genomic clone of murine CD8 (encoding Lyt-2.2) was excised from the pCA208 plasmid with the restriction enzyme Sal I and cloned into the Sal I site of the pSV2hph plasmid. The pCA208 plasmid is available from Dr. B. Mallison, INSERM-CNRS, Marseille, France. This plasmid contains a 4.5 Kb DNA insert encoding the Lyt-2.2 allele of murine CD8 that was originally cloned by Parnes. The pSVhph plasmid, available from Dr. P. Berg, Stanford University, CA, contains the hygromycin B phosphotransferase gene under the control of a SV40 promotor and enhancer, which provides a dominant selectable marker (resistance to hygromycin B) that does not interfere with subsequent selection of transfected cells in HAT medium.

The subcloning of CD8 into the pSV2hph plasmid was performed by standard methodolgies (Current protocols in molecular biology; Ed. Ausulbel, F. M., Brent, R., Kingston, R. W., Moore, D. D., Seidman, J. G., Smith, J. A., and Struhl, K. 1989, Wiley). Briefly, the plasmids pCA208 and pSV2hph were digested with Sal 1 enzyme in high salt buffer (100 mM NaCl). The CD8 insert and the linearized pSV2hph were purified by phenol/choloroform extractions and agarose gel electrophoresis. The linear pSV2Hph was treated with calf intestinal phosphatase. The CD8 insert was ligated to phosphatased pSV2hph with T4 ligase.

(b) Transformation of HB101 with SV2hph-Lyt-2.2.

Competent HB101 bacteria (purchased from BRL) were transformed with the pSV2hph-Lyt-2.2 plasmid by standard methodolgies (Current protocols in molecular biology; Ed. Ausulbel, F. M., Brent, R., Kingston, R. W., Moore, D. D., Seidman, J. G., Smith, J. A., and Struhl, K. 1989, Wiley). Briefly, competent HB101 were incubated with pSV2hph-Lyt-2.2 ligation mixture or plasmid on ice for 30 minutes and heated to 42° C. for 45 seconds. The mixture was then diluted with SOC media (J. Mol. Biol. 66: 557, 1983) and placed on ice for 2 minutes followed by incubation at 37° C. for 1 hour.

(c) Transfection of BW5147 with the gene encoding for Lyt-2.2.

The BW5147 tumor was then transfected with the thus prepared pSV2hphCD8 vector. Transfection was accomplished via spheroplast fusion. For the spheroplast fusions, log phase cultures (O.D.=0.5) of HB101 bacteria, transformed with the pSVShph/CD8 were cultured for 18 hours in 250µg/ml chloramphenicol. The amplified bacteria were then converted to spheroplasts, as described, for example, by Sandri-Goodin et al, "High frequency transfer of cloned herpes simples virus type 1 sequences to mammalian cells by protoplast fusion," *Mol. Cell Biol,*, 1:743 (1981), the pertinent portions of which are hereby incorporated by reference.

BW5147 cells were washed free of serum and $1.5 \times 10^6$ cells in 2.5 mls of serum-free DMEM media were incubated in 60 mm tissue culture dishes for 15 minutes at 37° C., during which time cells bind to the dish via discharge interaction. The spheroplast fusions were performed as described by Sandri-Goodin, cited above, by fusing the protoplasts to the BW5147 cells by treatment with polyethylene glycol as described.

The thus treated cells were harvested 48 hours after transfection and plated in microtiter plates at 105 cells per well in media containing 1.3-2 mg/ml hygromycin B (Sigma, St. Louis, Mo.) The hygromycin media was changed every 3–5 days.

Hygromycin resistant clones (transfectants) were identified at a frequency of 1 cell in $10^4$–$10^6$ cells. The hygromycin B-resistant clones were analyzed for expression of CD8 by indirect immunofluorescence and flow fluorocytometry. The hygromycin resistant cells were prepared for direct immunofluorescence as previously described by Rock, K. et al, "TAP, A novel T cell-activating protein involved in the stimulation of MHC-restricted T lymphocytes." *J. Exp. Med.* 315 (1986), using monoclonal antibody (MAb) containing supernatant followed by fluorescein isothiocyanate rabbit anti-mouse Ig (cross reactive with rat Ig). The MAb-containing supernatants were prepared from hybridomas HO2.2ADH4 (anti-Lyt-2.2) Gottlieb, et al, "Construction and properties of new Lyt-congenic strains and anti-Lyt-2.2 and anti-Lyt-3.3 monoclonal antibodies." *Immunogenetics* 10: 545 (1980); 53.6.3 (anti-Lyt-2,nonpolymorphic), Ledbetter, J. et al, "Xenogeneic monoclonal antibodies to mouse lymphoid differentiation antigens". *Immunol* Rev. 47: 362, 116.13 (anti-Lyt-2.1), GK1.5 (anti-CD4) Dialynas, et al, "Characterization of the murine antigenic determinants, designated L3T4a, recognized by monoclonal antibody GK1.5: Expression of L3T4a by functional T cell clones appears to correlate primarily with class II MHC antigen reactivity". *Immunol.* Rev. 74:29 (1983) and MKD6 (anti-IA$^d$) Kappler, J. et al, "Antigen inducible, H-2 restricted, interleukin-2 producing T cell hybridomas. Lack of independent antigen and H-2 recognition". *J, Exp. Med.* 153:1198 (1981). Fluorescence of 5,000 cells was quantified on a FACSCAN (Beckton Dickenson, Mountain View, Calif.) or EPICS V (Coulter Electronics, Hialeah, Fla.) flow cytometer. Transfectants expressing CD8 were detected, as is shown for a representative clone in FIG. 1.

Eight transfectants were analyzed for expression of CDS. Seventy-five percent (75%) of the transfectants analyzed expressed CDS. Five of six expressed high levels of CD8 (BW.CD8.3, BW.CDS.4, BW.CDS.6, BW.CD8.7, BW.CDS.8); one had minimal expression (BW.CDS.1).

Figure 1B:
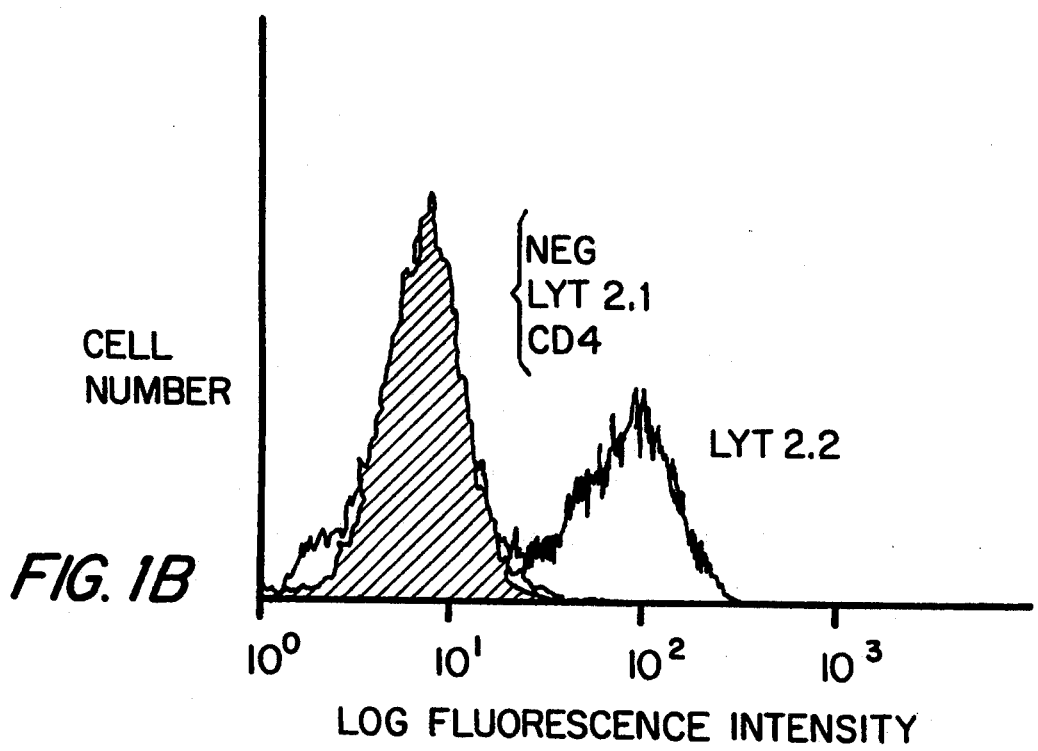

The BW5147 tumor is homozygous for the Lyt-2.1 allele of CD8, which is not expressed in BW5147. As shown in FIG. 1, the SV2hph-CD8 transfectants reacted with an anti-Lyt-2.2, but not an anti-Lyt- 2.1 monoclonal antibody, demonstrating that the CD8 expression arises from the transfected gene. This staining was specific, since control antibodies did not stain the transfectants and several anti-CD8 antibodies stained the transfected, but not the control, BW5147 cells. The expression of the CD8 molecules on the transfectants has been stable for months in the absence of hygromycin.

Representative clones expressing CDS, (BW.CDS.7 and BW.CDS.8), were selected for further study in the preparation of class I MHC restricted T-T hybridomas.

EXAMPLE 2

Hybridomas Derived From Fusions of Alloreactive T Cells With BW5147 or BW5147 Transfectants (a)-Preparation of alloreactive T cells.

C57BL/6 (H-2$^b$) T cells (responder cells) were obtained from C57BL/6 mice (Jackson Laboratory, Bar Harbor, Me.). Stimulator Balb/C (H-2$^d$) splenocytes were exposed to 1660 gamma irradiation with $^{137}$Cs source (Gamma Cell, Atomic Energy, Ltd, Canada). Responder T lymphocytes were enriched by nylon wool passage. $5 \times 10^6$ of the thus-prepared responder T lymphocytes were then cultured with an equal number of stimulator cells in a final volume of 1.5-2 mls in macrowells for 5 days at 37° C.

After 5 days, the cultures were tested for cytolytic activity in a conventional chromium release assay against $^{51}$Cr-labeled H-2$^d$ target cells. Target cells were obtained from the A20 cell line, which is a BALB/C, Ia+B lymphoblast cell line.

As expected and as shown in FIG. 5 D, these cultures exhibited strong cytolytic activity against the H-2$^d$ bearing targets. The viable cells from such cultures were then divided into aliquots and fused to either BW5147 or BW5147 CD8 transfectants.

(b) Fusion of alloreactive T cells with BW5147 or BW5147 CD8 transfectants.

The fusion of the alloreactive T cells obtained in accordance with the foregoing with BW5147 or BW5147 CD8 transfectants was conducted as follows. BW5147 cells, or BW5147 CD8 transfectants were mixed with the MLR stimulated C57BL cells as described in section (a) above, in a ratio of 4:1. The cells were washed three times with room temperature, serum-free, phosphate buffered saline (PBS), pH 7.4, at room temperature, after which the supernatant was decanted and the pellet respun by centrifugation. The tube was then warmed to 37° C., supernatant was aspirated and the pellet loosened by vigorous tapping. Pellets were resuspended in 1 ml 40% W/V polyethylene glycol (1400-1600 mw) at 37° C. and mixed for 45 seconds.

The thus obtained mixtures were then gradually diluted with 37° C. PBS and incubated at 37° C. for five minutes. Tubes were then subjected to centrifugation, and the supernatant was decanted and replaced with 50 ml PBS. The tubes were then inverted several times and centrifuged. The pellet were resuspended in complete media (Dulbecco's modified Eagle's medium, DMEM) at 37° C. DMEM with 4.5 g/liter glucose, 10% fetal calf serum and antibiotics was employed, which requires a $CO_2$ environment. Cells were distributed at about $2.5 \cdot 10^4$ in 100 μl per well in 96 well-flat bottom microwell test plates. After 24 hours of incubation at 37° C. the medium was replaced with 100 μl HAT-containing media at 37° C. and cultures were fed every 5-10 days with HAT medium.

When the hybrids had achieved a ½ to ¾ confluence, they were transferred to 1-2 ml macrowells in HAT medium. The macrowells were then passaged two times in HT medium before changing to regular medium.

In a first fusion, number 1 of Table 1, below, approximately 380 hybridomas per each individual fusion were produced. In another experiment, fusion number 2, approximately 90 hybridomas per individual fusion were produced.

(c) Screening for class I MHC-restricted alloreactive hybrids using lymphokine assay.

The resulting hybridomas were screened for their ability to produce lymphokines in response to the BALB/C lines M12 or M12.C3 M12 is an Ia+, B lymphoblastoid cell line that expresses both class I and class II MHC molecules. M12.C3 is an immunoselected variant of M12 which selectively lacks cell surface expression of Ia molecules, available from Dr. L. Glimcher, Harvard Medical School, Boston, Mass. For a description of this cell line, see Glimcher, L. H. et al, "Complex regulation of class II gene expression: Analysis with class II mutant cell lines.", *J. Immunol.* 135: 3542, (1985). By using these two cell lines, the specificity of the hybridomas could be defined as class I MHC-reactive (stimulated by both M12 and M12.C3) or class II MHC reactive (stimulated by M12 cells only). Reactivity was determined by the ability of the hybrid to produce lymphokines upon presentation of the specified cells.

The T-T hybridoma cultures were prepared for the screening for lymphokine production as previously described Rock, K. L. et al, 37 Inhibition of antigen-specific T lymphocyte activation by structurally related Ir gene-controlled polymers. Evidence of specific competition for accessory cell antigen presentation.", *J. Exp. Med.* 157:1618, (1983). To summarize, microcultures were prepared with $5-10 \times 10^4$ of the T-T hybrids in the presence or absence of $5 \times 10^4$ M12 or M12/C3 cells in 200 μl flat bottom microliter wells in duplicate. The culture constituents were RPMI 1640 supplemented with 4mM L-glutamine, 1X nonessential amino acids, 2.38 μg/ml HEPES buffer, 100 units/ml penicillin, 100 mcg/ml streptomycin, 0.25 mcg/ml of fungizone, $5 \times 10^{-5}$ M beta mercaptoethanol and 10% fetal calf serum. After 18–24 hours incubation at 37° C., a 100 μl aliquot of supernatant was removed and assayed for lymphokine content.

The lymphokine content (IL-2) in the T cell hybridoma culture supernatants was measured with a quantitative bioassay with HT2 cells as previously described. Kappler, J. et al, "Antigen inducible, H-2 restricted, interleukin-2 producing T cell hybridomas. Lack of independent antigen and H-2 recognition". *J. Ext. Med.* 153:1198 (1981). Using this methodology, 100 μl of the supernatant prepared as described above was harvested and exposed to 8,000 rads gamma irradiation. IL-2 content was measured by adding $5 \times 10^3$ IL-2 dependent cells (HT2) and incubating for 20–26 hours, with 1 μl of tritiated thymidine added over the last 4–6 hours. The cultures were then harvested on glass fiber filter strips with the aid of a semi-autonomated cell harvester (PHD cell harvester, Cambridge Technology Co., Cambridge, Mass.) and the incorporation of label into DNA determined by scintillation counting. In general, the concentration of IL-2 measured in the culture supernatant was limiting.

The response of two representative hybridomas (BW5147.CDS.7.4 and BW5147.CDS.7.11), which illustrate the two patterns of MHC reactivity, are displayed in Table IA. Data are displayed as the arithmatic mean counts per minute (CPM) for duplicate cultures. Table 1B summarizes the frequency of hybridomas responding to the two stimulator cells (M12 and M12C3). Responses were scored as positive if they were >3x the medium control (90% of the responses were >10x over the background). Hybrids that responded to M12 and M12/C3 are listed as class I MHC reactive and those that responded to only M12 are listed as class II MHC-reactive. Hybridomas arising in fusion 2 were assayed on two different days (Experiments 1 & 2).

TABLE I

Reactivity of Hybridomas Derived From Fusions Between MLR Activated T Cells and BW5147 Versus BW5147-CD8 Transfectants A. Representative Patterns of Reactivity

| Hybrid | Stimulator | (Phenotype) | CPM $\times 10^{-3}$ |
|---|---|---|---|
| BW.CD8.7.4 | None | | 0.2 |
| | M12.C3 | (Ia−) | 86.4 |
| | M12 | (Ia+) | 54.5 |
| BW.CD8.7.11 | None | | 0.2 |
| | M12.C3 | (Ia−) | 0.2 |
| | M12 | (Ia+) | 71.6 |

B. Summary of Hybridoma Reactivity

| | Class I MHC | Class II MHC |

TABLE I-continued

Reactivity of Hybridomas Derived From Fusions Between MLR Activated T Cells and BW5147 Versus BW5147-CD8 Transfectants

| Fusion # | Exper. # | Fusion Partner | # Hybrids Examined | Reactive # | Reactive % | Reactive # | Reactive % |
|---|---|---|---|---|---|---|---|
| 1 | 1 | BW5147 | 41 | 1 | 2 | 5 | 12 |
| 1 | 1 | BW.CD8.7 | 40 | 7 | 18 | 13 | 33 |
| 1 | 1 | BW.CD8.8 | 40 | 7 | 18 | 7 | 18 |
| 2 | 1 | BW5147 | 18 | 1 | 5 | 5 | 28 |
| 2 | 1 | BW.CD8.7 | 38 | 9 | 24 | 6 | 16 |
| 2 | 2 | BW5147 | 13 | 1 | 8 | 0 | 0 |
| 2 | 2 | BW.CD8.7 | 19 | 0 | 0 | 2 | 11 |
| 1 + 2 | | BW5147 | 72 | 3 | 4 | 10 | 14 |
| 1 + 2 | | BW-CD8 transfectants | 137 | 23 | 17 | 22 | 16 |

Several points about the results should be noted. First, the BW5147 CD8+transfectants give rise to a significantly higher frequency of class I MHC-restricted hybridomas, as compared to the untransfected BW5147 untransfected cell. This significantly higher frequency is important, since the potential for the successful isolation of hybrid clones depends upon both the ease of hybrid detection and the frequency of the desired cell type in the population being fused. The BW5147.CD8 transfectants clearly give rise to a significantly higher frequency of hybrids, and are thus better than the BW5147 fusion hybrids alone. Second, this increased frequency of the class I MHC-restricted hybrids is observed with two independent CD8 transfectants. This indicates that the increased frequency of class I reactive hybrids is related to the expression of the transfected gene and does not reflect random variation in the activity of the BW5147 subclones. This point will be further emphasized in monoclonal antibody blocking experiments described below. Third, these results demonstrate that it is possible to detect lymphokine-producing class I MHC-restricted hybridomas prepared with BW.CD8.

A representative alloreactive class I MHC-restricted hybrid, BW5147.CD8.7.4, was deposited with the ATCC, Parklawn Drive, Rockville, Md. on Mar. 14, 1990 and has been assigned ATCC accession number HB10385.

EXAMPLE 3

Generation of Antigen-Specific, Class I MHC-Restricted lymphokine-Producina T-T Hybridomas This example demonstrates that the BW5147 transfectants of the present invention can also be used to generate antigen-specific T-T hybridomas.

(a) Preparation of antigen-specific cytotoxic T-lymphocytes.

A source of antigen-specific, cytotoxic T lymphocytes was generated by a modification of the method of Carbone et al, "Class I restricted processing and presentation of exogenous cell-associated antigen in vivo", *J. Exp. Med.*, 171:377, (1990). In accordance with this method, unfractionated splenocytes were incubated with 10 mg/ml OVA in RPMI for 10 minutes at 37° C., washed and exposed to 3000 rads gamma irradiation. Thirty to forty million of such splenocytes were injected intravenously into C57BL/6 mice. Seven days later spleens were removed. Spleen cells were boosted for 5 days in culture with irradiated EG7 in accordance with the procedure of Moore et al, "Introduction of Soluble Protein into the class I Pathway of Antigen Processing and Presentation", Cell, Vol. 54, pp. 777–785, (1988), the pertinent portions of which are incorporated by reference. The resulting cells were then tested for their ability to lyse antigen bearing target cells.

Cytotoxic cells capable of lysing EG7, the OVA-transfected EL4, target cells but not the parental line (e.g. EL4) were readily detectable in these cultures as shown in FIG. 5. Cytolytic activity was tested against $^{51}$Cr-labeled EL4, EG7 or A20 as follows. The target cells for the lytic assays were incubated with 20 μCi/ml of sodium ($^{51}$Cr) chromate for 18–24 hours at 37° C. Washed $^{51}$Cr-labeled target cells, (2×10$^4$) were co-cultured with a serial dilution of effector cells in 200 μl of media. The precise effector to target ratios were 100:1, 33:1 and 11:1. After 4 hours of incubation at 37° C., the culture supernatant was collected and counted in a gamma counter (Beckman Instruments, Fullerton, Calif.). The percent specific lysis was calculated as follows.

% specific lysis = (Experimental release − spontaneous release)/ (Maximum release − spontaneous release) × 100.

Maximum release was determined by lysis with 1% SDS. Spontaneous release was generally less than 15% of maximum release.

(b) Fusion of BW5147 or BW5147.CD8 transfectants with OVA-specific cytotoxic T cells and screening for the production of lymphokines.

The responding T cells which exhibited OVA-specific CTL activity were fused with the BW.CDS.7 transfectant clone and cultured in HAT medium as described in Example 2 above. Approximately 278 hybrids were obtained from the fusion. Some of the hybridomas obtained from the fusion, were then screened for the production of lymphokines, as described in Example-2, with the following deviations. The microcultures were prepared with 10$^5$ of the T-T hybrids and either a titration of 0.6–10×10$^4$ of EL4 or EG7 antigen presenting cells per well or 5×10$^4$ EL4 cells in the presence or absence of a titration of 0–100 mg/ml tOVA, which is a trypsin digest of OVA prepared as described by Shimonkevitz, J. Exp. Med., 158:303 (1983). The culture constituents were as previously described. After 18–24 hours incubation at 37° C., a 100 μl aliquot of supernatant of the cultures was removed and assayed for lymphokine content as described in Example 2.

Figure 2A:
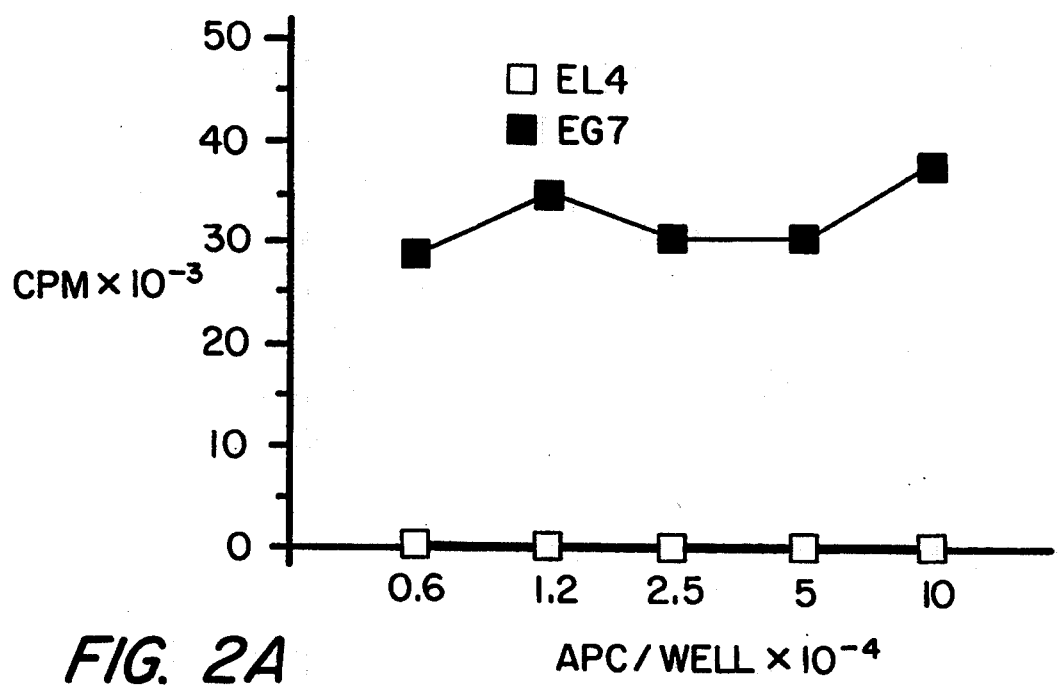
FIGS. 2 A and B are graphical representations which illustrate the antigen reactivity of a representative OVA-specific, class I MHC-restricted T-T hybridoma in the lymphokine assay. Microcultures were prepared with $10^5$ RF33.70 cells (a C57BL/6 anti-OVA $+K^b$ X BW.CD8.7, T-T hybridoma) and either the indicated titration of EL4 or EG7 (a clone of EL4 transfected with an OVA cDNA) cells (FIG. 2A) or $5 \times 10^4$ EL4 cells in the presence or absence of the indicated titration of a complete trypsin digest of ovalbumin (tOVA) (FIG. 2 B).
Figure 2B:
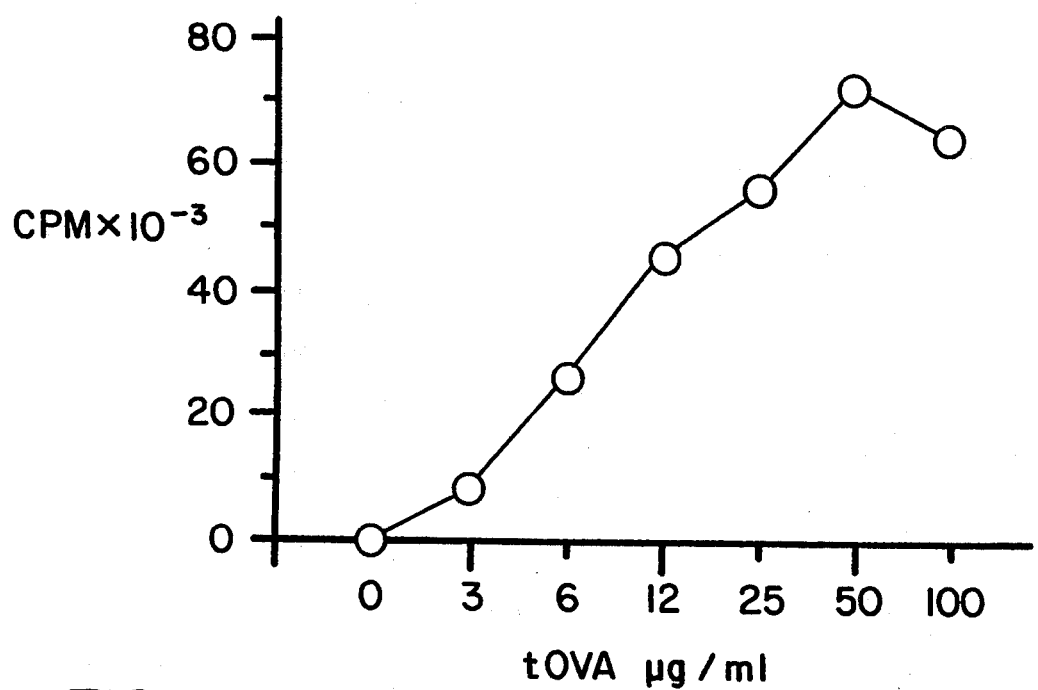

Several lymphokine-producing hybridomas were identified (7 of 124 screened). Those hybrids that reacted strongly were identified as RF33.21, RF33.44, RF33.55 and RF33.70. The antigen reactivity of one representative OVA-specific, class I MHC-restricted T-T hybrid, designated RF33.70 (a C57BL/6 anti-Ova +K$^b$×BWCDS.7 T-T hybridoma) is provided in FIG. 2. These cells produce lymphokines in response to EG7, but not EL4 cells. Since EL4 and EG7 differ only in the expression of the OVA gene, this result indicates that the hybrids are OVA-specific. To further assess the specificity of these hybrids, they were stimulated with a tryptic digest of OVA (tOVA) in the presence of EL4 cells. As shown in FIG. 2, the hybrids respond to tOVA. RF33.70 does not respond to tOVA in the absence of antigen presenting cells in the culture. Together, these results demonstrate that these hybridomas are specific for OVA.

To further analyze the specificity of the RF33 hybridomas, they were tested for their responsiveness to tOVA in the presence of APC's from MHC congenic mice. Microcultures were prepared with:

10$^5$ RF33.21 (a C57BL/6 anti-Ova+K$^b$×BWCD8.7 hybridoma);

10$^5$ RF33.70 (a C57BL/6 anti-Ova+K$^b$×BWCD8.7 hybridoma); or

5×10$^4$ 8DO.51.15 (a BALB/C anti-Ova+IA$^d$×BW5147 hybridoma) with a source of antigen-presenting cells (APC's) and with or without 100 μg/ml tOVA.

APC's were EL4 cells (5×10$^4$/well), WOP3027 cells (2×10$^5$/well) WOP/K$^b$ cells (2×10$^5$/well) or LPS blasts (2×10$^5$/well) from the indicated mice strains. The 8DO.51.15 hybridoma is available from Drs. Kappler and Marrack (National Jewish Center, Denver, Colo.). WOP3027 is a polyoma transformed, NIH 3T3 cell line, available from C. Basilico (New York University, N.Y. , N.Y.). The WOP/K$^b$ is a WOP3027 fibroblast cell line which has been transfected in a manner to allow expression of the K$^b$ gene. The cultures were handled as previously described. The analyses are set forth in Table II.

TABLE II

Analysis of the MHC Specificity of OVA Reactive Hybridomas

| Exp. | Hybrid | Ag | APC | K, I, and D | CPM × 10$^{-3}$ |
|---|---|---|---|---|---|
| 1 | RF33.21 | − | B10 | b b b | 0.6 |
|  |  | + | B10 | b b b | 132.6 |
|  |  | − | B10.D2 | d d d | 0.4 |
|  |  | + | B10.D2 | d d d | 0.3 |
|  |  | − | B10.HTG | d d b | 8.7 |
|  |  | + | B10.HTG | d d b | 4.5 |
|  |  | − | B10.A3R | b b/k d | 1.5 |
|  |  | + | B10.A3R | b b/k d | 132.4 |
|  |  | − | EL4 | b — b | 2.8 |
|  |  | + | EL4 | b — b | 76.5 |
| 1 | 8DO51.15 | − | B10 | b b b | 0.3 |
|  |  | + | B10 | b b b | 0.3 |
|  |  | − | B10.D2 | d d d | 1.1 |
|  |  | + | B10.D2 | d d d | 150.8 |
|  |  | − | B10.HTG | d d b | 0.2 |
|  |  | + | B10.HTG | d d b | 151.1 |
|  |  | − | B10.A3R | b b/k b | 0.8 |
|  |  | + | B10.A3R | b b/k b | 0.4 |
|  |  | − | EL4 | b — b | 0.3 |
|  |  | + | EL4 | b — b | 0.2 |
| 2 | RF33.21 | − | WOP3027 | — | 0.6 |
|  |  | + | WOP3027 | — | 0.5 |
|  |  | − | WOP/K$^b$ | K$^b$ | 0.3 |
|  |  | + | WOP/K$^b$ | K$^b$ | 43.5 |
| 2 | RF33.70 | − | WOP3027 | — | 1.6 |
|  |  | + | WOP3027 | — | 0.7 |
|  |  | − | WOP/K$^b$ | K$^b$ | 0.8 |
|  |  | + | WOP/K$^b$ | K$^b$ | 33.7 |

In experiment 1 the presence (letters) or absence (—) of the expressed K, I D MHC allelic gene products are indicated. In experiment 2, the presence (K$^b$) or absence (—) of the transfected and expressed K$^b$ is indicated.

As shown in Table II, the T-T hybrids are stimulated by tOVA in the presence of APC's from B10 mice (H-2$^b$) but not APC's from other MHC congenic strains, eg. B10.D2 (H-2d), indicating that the OVA-reactive hybrids are MHC-restricted. When APC's from recombinant inbred mice were tested, those that express K$^b$, IA$^b$ (B10.A3R) supported the OVA response, whereas APC's that expressed only D$^b$ (B10HTG) did not (Table II). In contrast, the B10.D2 and B10HTG APC's are capable of stimulating the OVA+IA$^d$ specific hybrid, 8D051.15, which serves as a positive control for their antigen presenting activity. Since the IA negative EL4 and EG7 cells present antigen to the RF33 hybrids, these hybridomas are not restricted by class II molecules. Taken together, these results indicate that the OVA-specific hybrids are restricted by H-2K$^b$.

To verify this conclusion, the K$^b$ gene was transfected and expressed in WOP3027 fibroblasts and these cells were tested for their ability to present antigen to the RF33 hybrids. As shown in Table II the transfected WOP/K$^b$ cells present tOVA to the RF33 hybrids, whereas the untransfected control cells do not.

A representative antigen-specific class I MHC-restricted hybrids, RF33.70 was deposited with the ATCC, 12301 Parklawn Drive, Rockville, Md., on Mar. 14, 1990 and has been assigned ATCC accession number HB10386.

On the basis of the foregoing results, it can be seen that the present invention can be used to generate antigen-specific, class I, MHC restricted T-T hybridomas. The alloreactive T cells that arise in MLRs are comprised of T cells that bear a diverse spectrum of antigen specific T cell receptors that cross react with allogenic MHC. Since a high frequency of alloreactive T-T hybridomas are generated from these cells, and since OVA reactive T-T hybridomas are generated from OVA stimulated T cells, the present invention is generally applicable and should allow for the generation of functional hybridomas from T cells specific for virtually all antigen/class I MHC specificities.

EXAMPLE 4

Phenotype of the Class I MHC-Restricted Hybridomas

The cell surface phenotypes of the OVA-specific hybrids and the alloreactive hybrids that were derived from BWCD8 transfectants and of alloreactive hybrids derived from nontransfected BW5147 were determined as follows. The cells were prepared for indirect immunofluorescence staining with anti-CD8 monoclonal antibodies (anti-Lyt-2.2, anti-lyt 2 nonpolymorphic and anti-Lyt-2.1) and with anti-CD4 monoclonal antibodies, employing the procedures described by Rock, K. et al, in "TAP, A novel T cell-activating protein involved in the stimulation of MHC-restricted T lymphocytes". *J. Exp. Med.* 315 (1986). Monoclonal-antibody containing supernatants were prepared from the hybridomas HO2.2ADH4 (anti-Lyt-2.2), 53.6.3 (anti-lyt nonpolymorphic), 116.13 (anti-Lyt-2.2), GK1.5 (anti-CD4) MKD6, and HP25. In some cases, culture supernatants were dialyzed against RPMI 1640. MAbs were purified from culture supernatant or ascites by affinity chromatography on protein A or protein G columns.

The aforementioned hybrids were incubated with the anti-CD8 and anti-CD4 antibodies, followed by FITC-anti Ig and analyzed by flow fluorocytometry. Fluorescence was analyzed on a FACSCAN flow cytometer and data were displayed as cell number on the ordinate vs. log relative fluorescence intensity on the abscissa. The background (NEG) curve is hatched, other curves are unshaded. The background curve was prepared by incubating the hybrids with MKD6 followed by FITC anti-Ig. MKD6 is a control Mab of unrelated specificity.

Figure 3A:
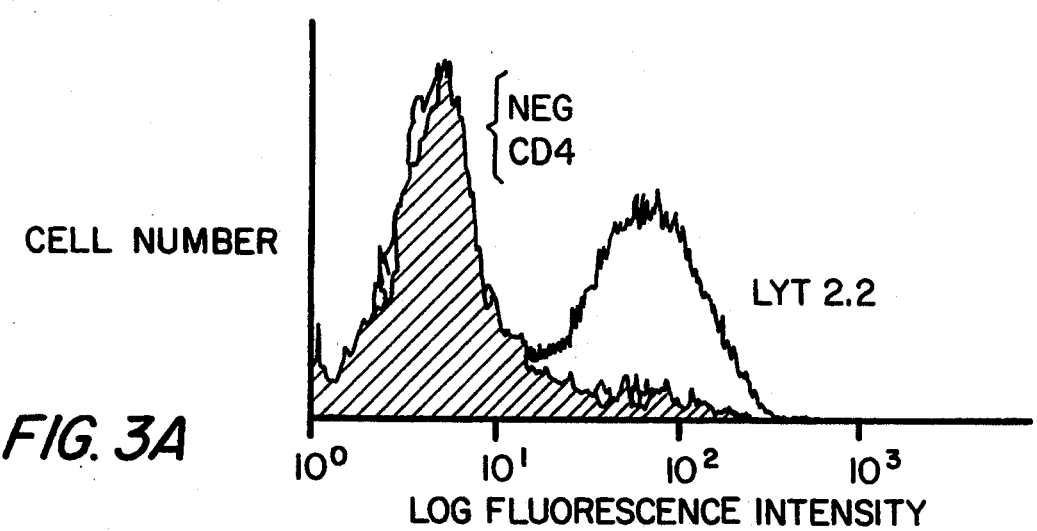
FIGS. 3A, B, and C are fluorescent histograms from the flow cytometric analysis for cell surface phenotype of class I MHC-restricted T-T hybridomas. The following T-T hybridomas were prepared for indirect immunofluorescence and analyzed by flow fluorocytometry.
Figure 3B:
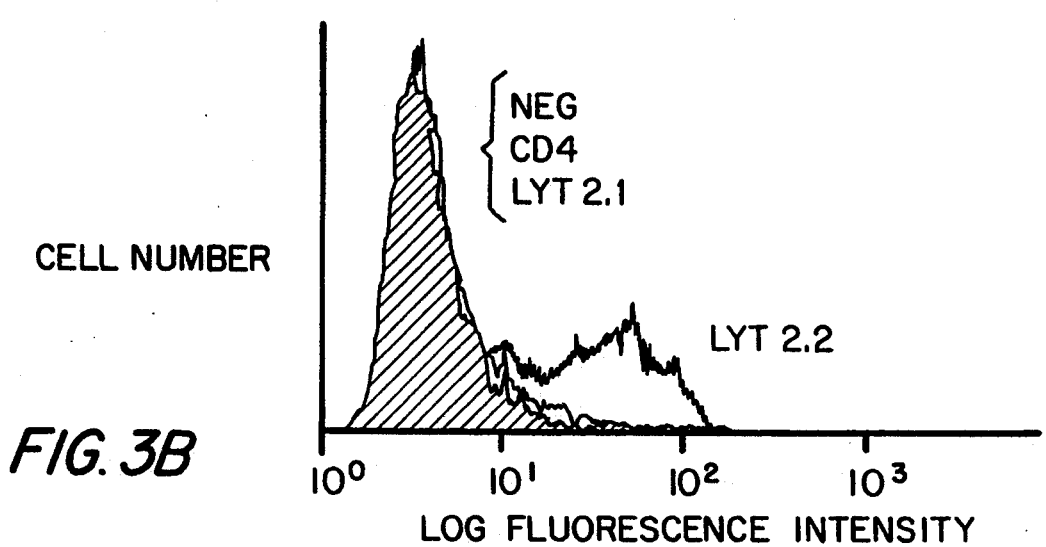
(FIG. 3 B): A C57BL/6 anti-class I, H-$2^d$ alloreactive X BW.CD8.7 T-T hybridoma (CD8.7.4)
Figure 3C:
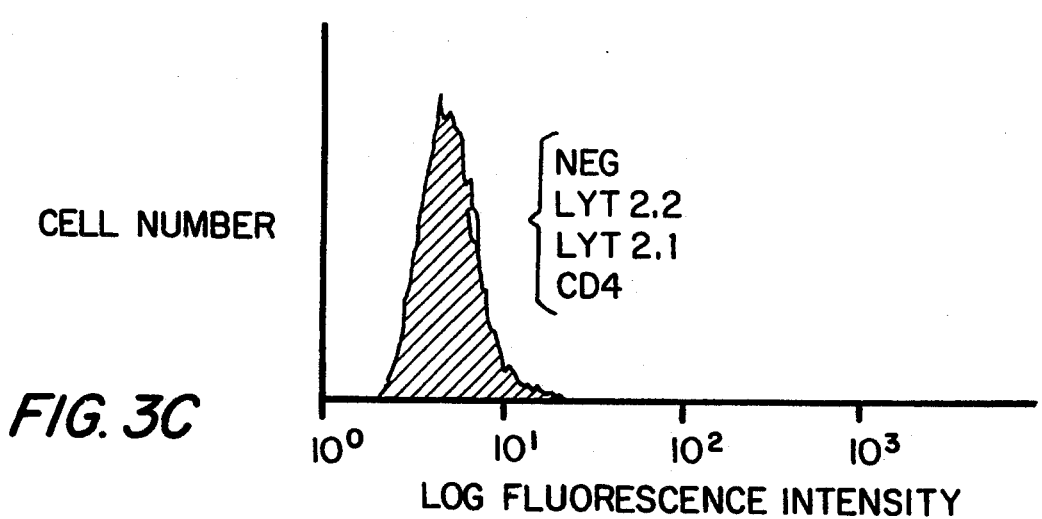

The fluorescence histograms of several representative clones are shown in FIG. 3. Both the OVA-specific (FIG. 3A) and the alloreactive hybrids (FIG. 3B) that are derived from the BW5147-CD8 transfectants express CD8 molecules. The CD8 molecules that are expressed on these cells bear the Lyt-2-2 allelic polymorphism. In contrast, the alloreactive hybrids derived from BW5147 do not express CD8 and CD4 molecules (FIG. 3C). The staining with these MAbs is specific since they do not react with CD8- or CD4 negative cells (FIGS. 1A and 3C). In addition, the T-T hybrids do not stain with irrelevant mAbs (FIG. 3). Expression of CD4 molecules was not detected on the hybridomas described above (FIG. 3), which suggests that they arose from fusions with CD4 negative T cells. CD4 is present on most class II MHC-restricted hybrids.

EXAMPLE 5

Role of CD8 on Class I MHC-restricted T-T Hybridomas

Figure 4A:
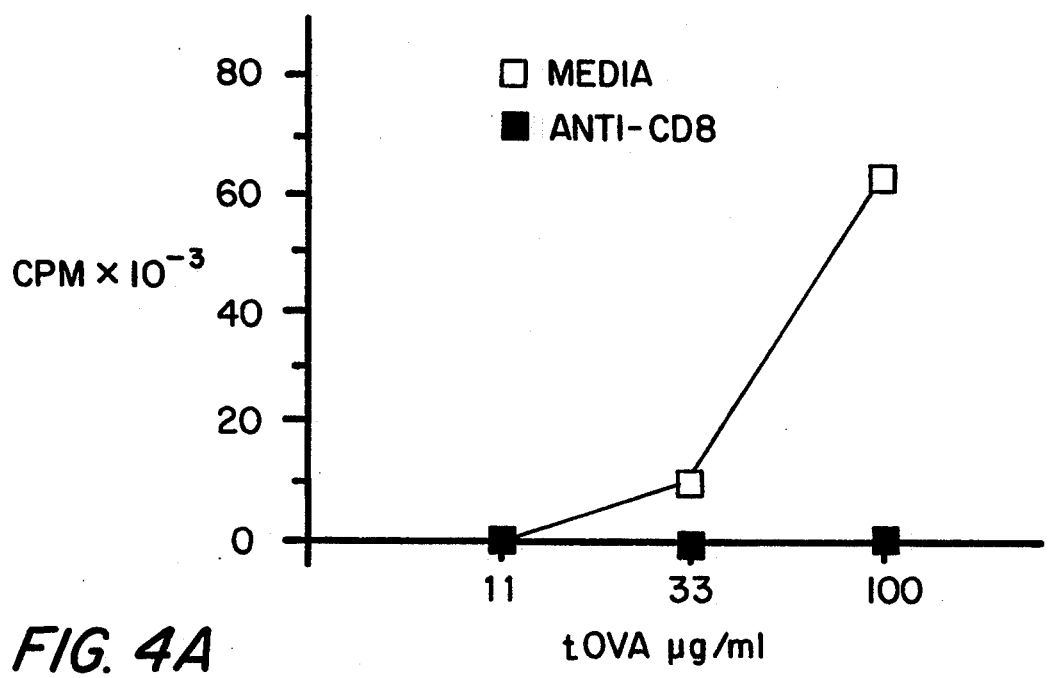
FIGS. 4, A, B, C, D, and E are graphical representations which illustrate the effect of anti-CD8 MAb on the stimulation of representative OVA-specific, class I MHC-restricted T-T hybrids. Microcultures were prepared with $10^5$ of the following T-T hybridomas: RF33.70 (OVA+$K^b$ specific, CDS+) (FIG. 4, A and B); RF33.21 (OVA +$K^b$ specific, CDS+) (FIG. 4, C and D) or 79.I.39 (alloreactive, $D^d$ specific, CD8-) (FIG. 4, E). The hybridomas were cultured with or without the indicated titration of tOVA in the presence of $5 \times 10^4$ EL4 cells (as a source of APCs) (FIG. 4, A and C) or with the indicated titration of CON A in the absence of APCs (FIG. 4, B and D) or with the indicated titration of A20 APCs (FIG. 4, E). Where indicated, the following MAb preparations were added to culture: a 1:16 dilution of 53.6.3 culture supernatant (anti-CDS), 10 μg/ml MKD6 (anti-IA), 10 μg/ml HP25, and a 1:8 dilution of M5/114 (anti-Ia) culture supernatant.
Figure 4B:
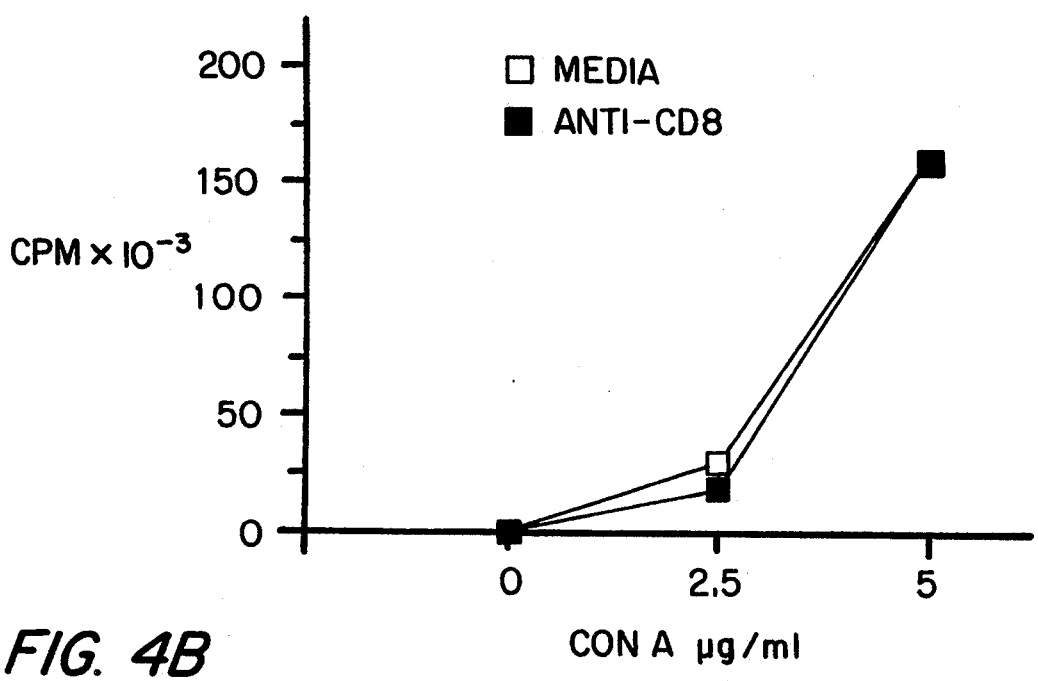
Figure 4C:
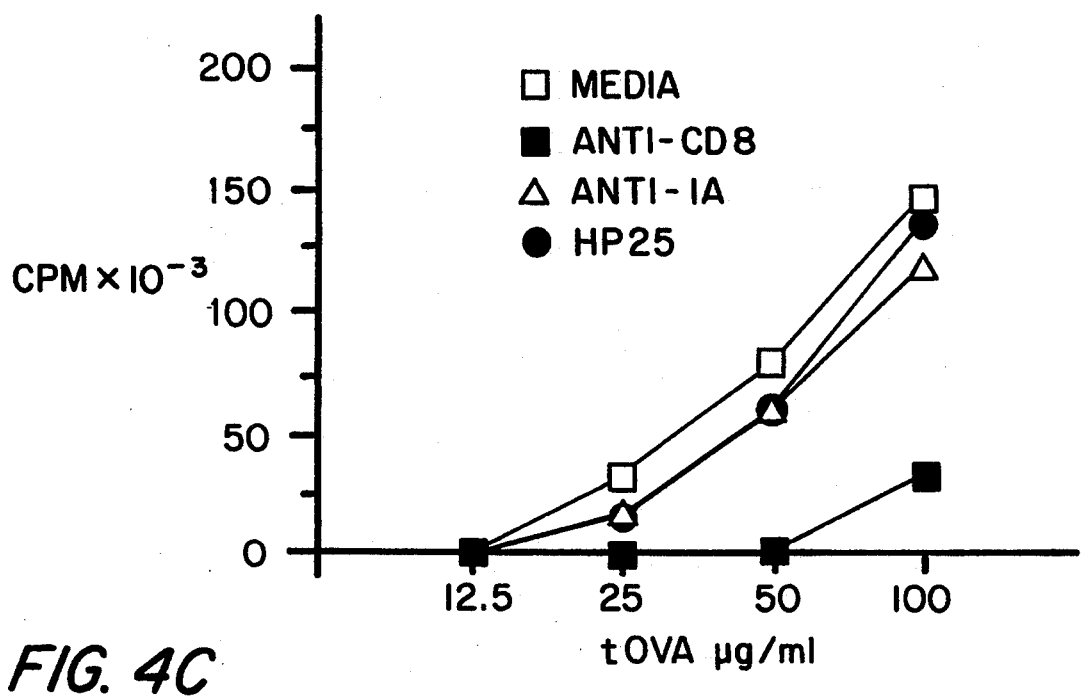
Figure 4D:
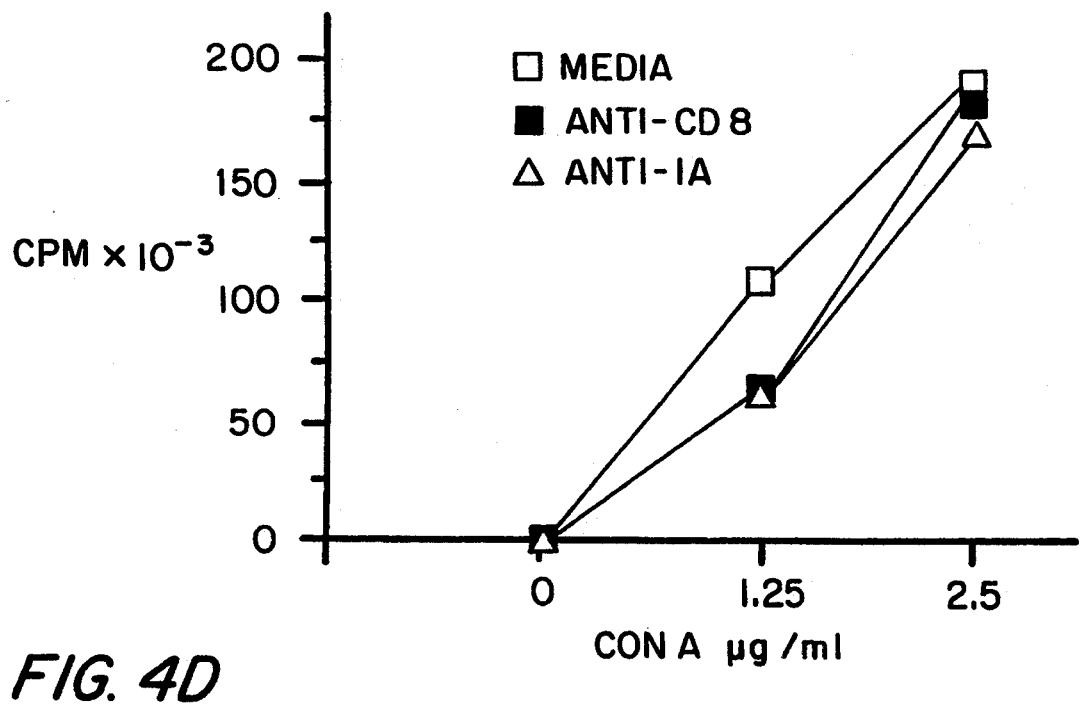
Figure 4E:
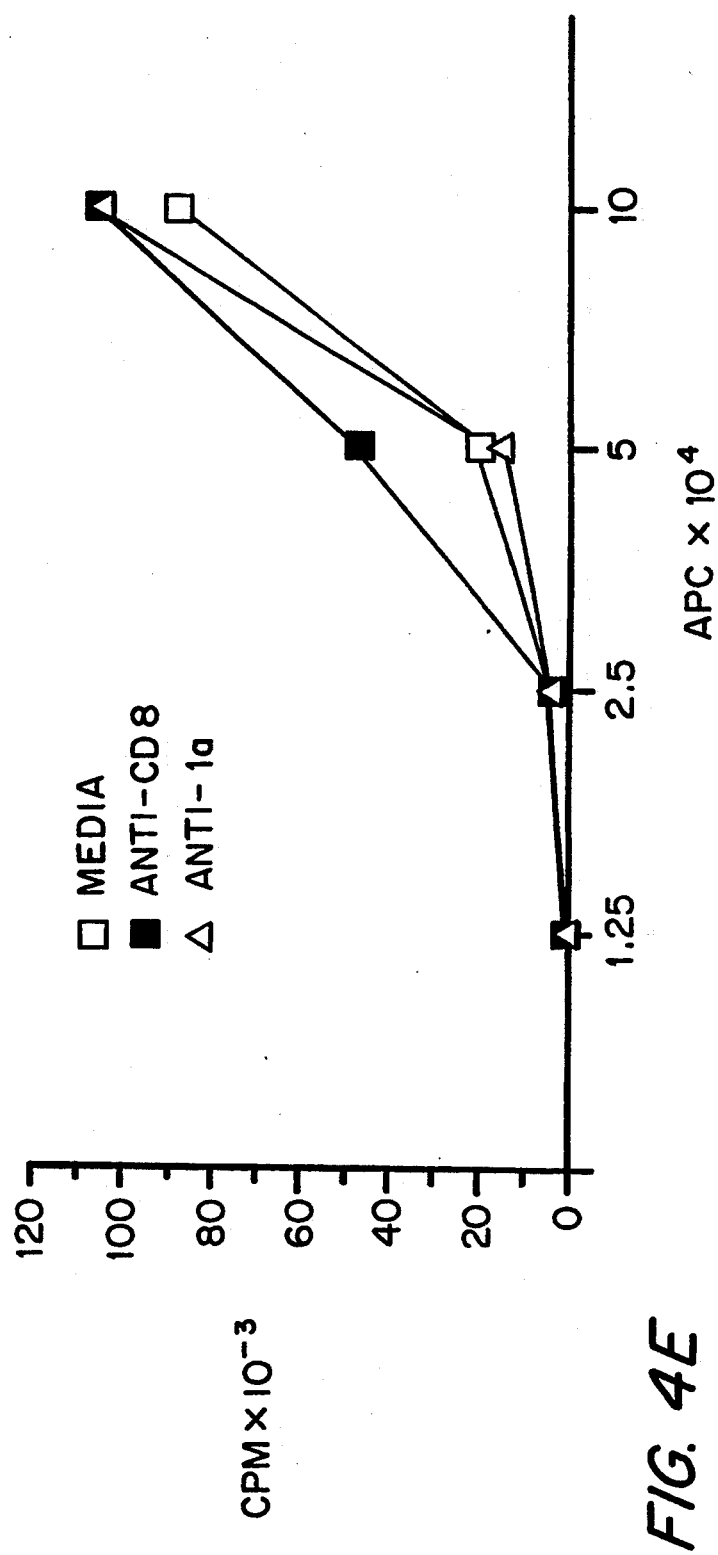

To assess the functional significance of the CD8 molecules on the class I MHC-restricted T-T hybridomas, we tested the effects of anti-CD8 MAbs on their stimulation. As shown in FIG. 4A and C, anti-CD8 markedly inhibits the stimulation of two OVA-specific hybridomas by tOVA with EL4 APCs. Similar results have been obtained for another hybridoma (RF33.44) with the same specificity. This inhibition is specific, since mAbs of an irrelevant specificity (MKD6) or MAbs that bind other structures on T cells (HP25) do not effect the stimulation (FIG. 4C) Moreover, the anti-CD8 MAb does not inhibit the stimulation of a CD8 negative alloreactive T-T hybrid (FIG. 4E). Finally, the same anti-CD8 MAb does not inhibit the stimulation of the OVA-specific hybrids by the mitogen, CON A (FIG. 4B and 4D). This latter result also suggests that the anti-CD8 MAb inhibition is due to blocking of CD8 function rather than from the induction of a "negative signal". Taken together, these results indicate that CD8 molecules play a critical role in the antigen/APC driven activation of the OVA-specific, class I MHC-restricted, T-T hybrids.

EXAMPLE 6

Cytolytic Capacity of the Class I MHC-restricted T-T Hybridomas

Figure 5A:
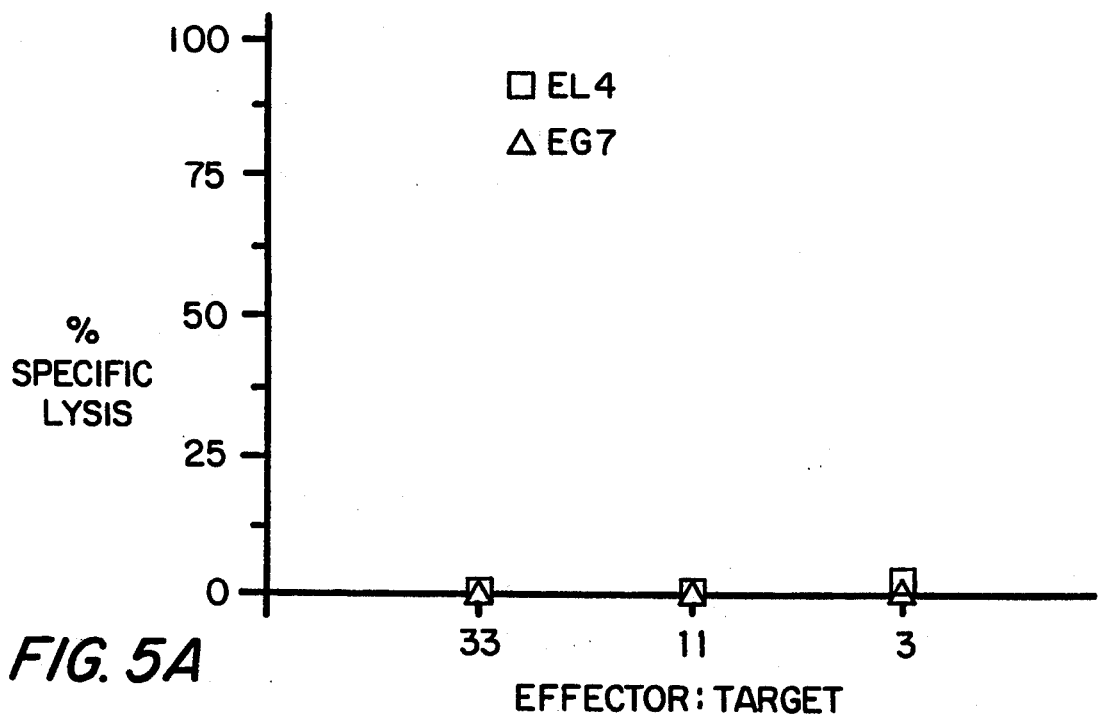
FIGS. 5, A, B, C, and D are graphical representations which illustrate that the class I MHC-restricted T-T hybrids did not mediate antigen-specific cytolysis. RF33.70 (an OVA+$K^b$ specific T-T hybridoma) (FIG. 5, A), OVA primed and restimulated C57BL/6 splenocytes (FIG. 5, B), CD8.7.4 (an alloreactive, anti-H$2^d$ class I specific T-T hybrid) (FIG. 5, C) or C57BL/6 anti-BALB/C alloreactive MLR T cells (FIG. 5,D) were tested for cytolytic activity against $^{51}$Cr-labeled EL4, EG7 (EL4 transfected with an OVA cDNA) (FIG. 5, C and D) cells.
Figure 5B:
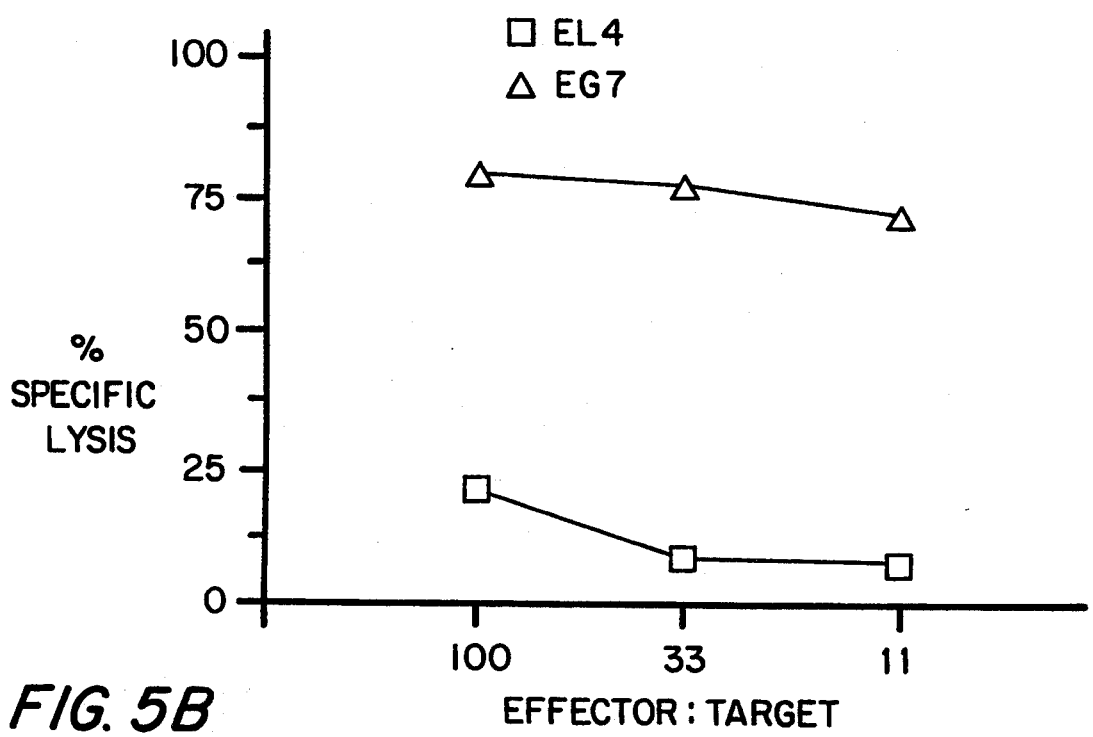
Figure 5C:
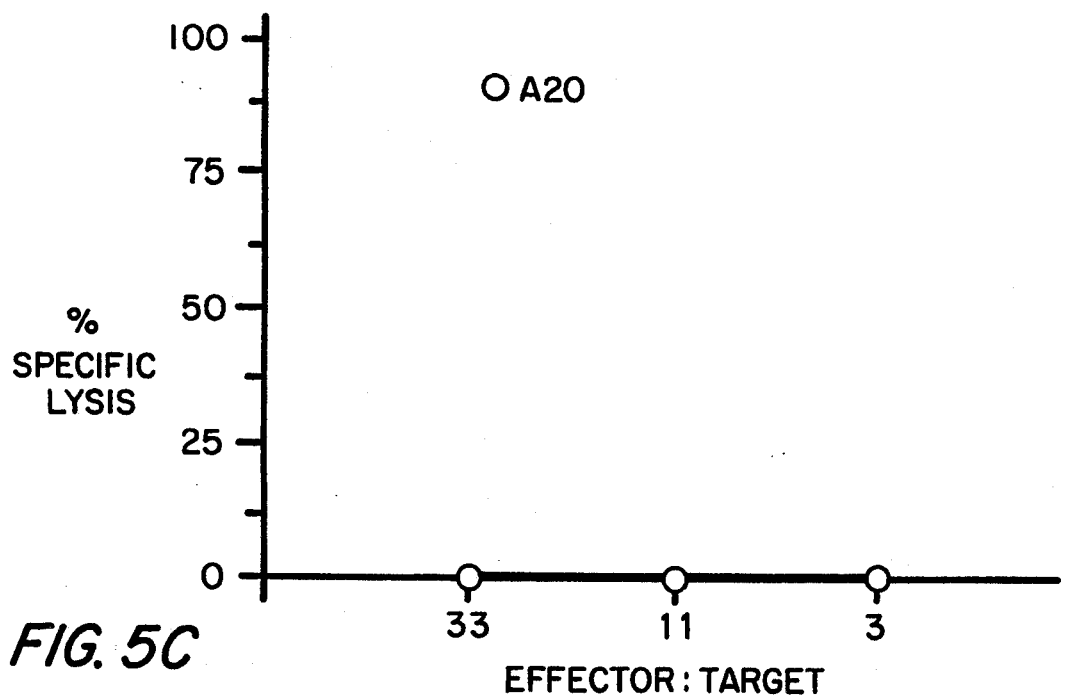
Figure 5D:
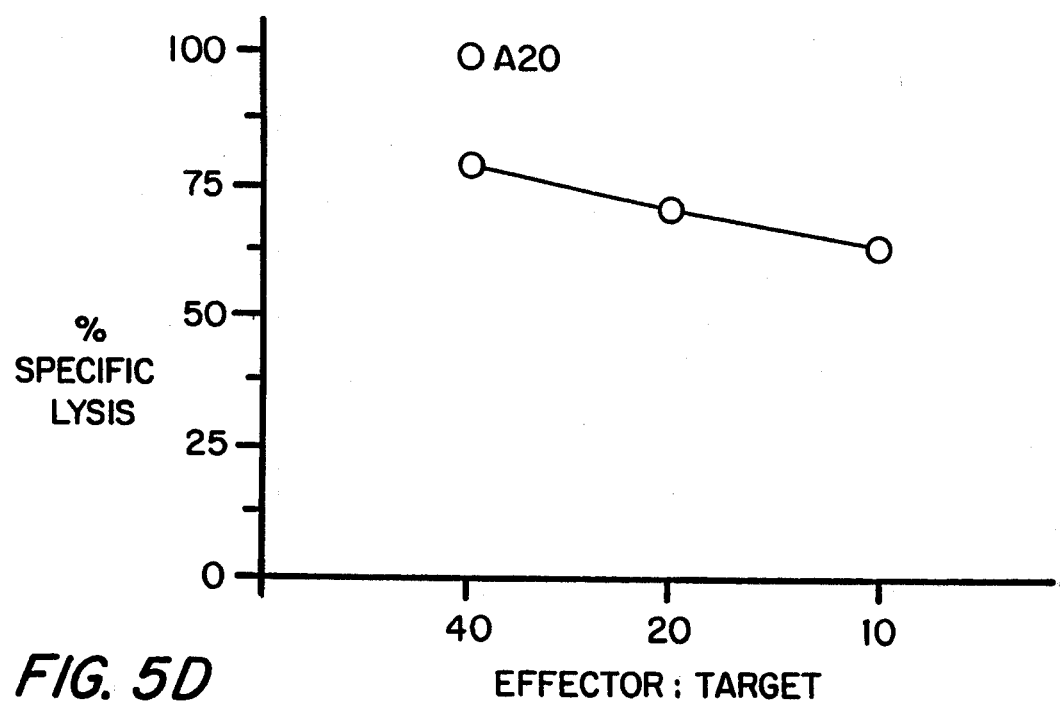

This example seeks to establish whether the class I MHC-restricted T-T hybrids exhibit cytolytic activity, since it is likely that these hybrids arise from a fusion between an antigen-specific CTL and the BW5147-CD8 transfectant. To test this point, the OVA-specific T-T hybrids were incubated with $^{51}$Cr loaded EL4 or EG7 cells. As shown in FIG. 5A, no specific release of $^{51}$Cr was detected for the two T-T hybrids tested. In contrast, the EG7, but not EL4, cells are killed by polyclonal OVA-specific CTL (FIG. 5B). Similarly, two class I MHC-specific, alloreactive cells were tested for their ability to lyse A20 cells, and cytolytic activity was not detected (FIG. 5C). The A20 cell does, however, stimulate the alloreactive T-T hybrids to produce lymphokines (FIG. 4) and it is a sensitive target cell for polyclonal, alloreactive CTL (FIG. 5D).

One of the differences between the present invention and previous studies is the use of a lymphokine assay to detect class I MHC-restricted hybridomas instead of the standard lytic assay. This difference is critical for the identification of the class I MHC-restricted hybrids, because it has been found that the cells isolated did not have activity in lytic assays, as shown above. Accordingly, BW5147 may not be generally permissive for cytolytic function. It should be noted, however, the fusions were not screened for lytic activity and it is possible that hybrids with CTL activity constitute a distinct subpopulation of clones.

EXAMPLE 7

This example describes the preparation of another antigen-specific T-cell-T-cell hybrid.

Splenocytes from influenza immune C57BL/6 mice (Jackson Laboratories) were stimulated with virus-infected syngeneic cells in vitro, substantially as described in Example 3. Mice were injected intraperitoneally with allantoic fluid (100 μl) from influenze virus-infected eggs. In vitro secondary anti-influenza cytotoxic T lymphocytes were prepared essentially as described.

Briefly, after about >3 weeks of immunization, influenza-immune splenocytes (30×10$^6$) were co-cultured with influenza-infected splenocytes (15-20×10$^4$) in 15 ml. of medium in upright 25-cm$^2$ flasks and were incubated for 5-6 days at 37° C. The cells were then harvested from culture and incubated with $^{51}$Cr-labeled target cells (2×10$^4$) at effector to target ratios of 100:1, 33:1 and 11:1. After 4 hours at 37° C., the culture supernatant was harvested and the $^{51}$Cr released was measured in a gamma counter.

The responding T-cells that exhibited influenza-specific cytolytic activity were fused to the BW CD8.7 transfectant clone using the fusion protocol described in Example 3. Some of these hybrids were then screened for their ability to produce IL-2 when stimulated with NP365-380 and syngeneic APC EL4 cells in fetal calf serum-containing medium. NP 365-380 is a synthetic peptide corresponding to amino acid residues 365-380 of the influenza nucleoprotein (1968 strain) that was synthesized by the Molecular Biology Core facility at the Dana-Farber Cancer Institute (Boston, Me.). NP 365-380 is an immunodominant epitope recognized by T-cells of H-2$^b$ mice and was one of the first examples of a class I MHC restricted peptide capable of sensitizing target cells. This peptide is present in associated with D$^b$ molecules. Screening of the hybrid cells was conducted as described in Example 3.

Briefly, duplicate microcultures were prepared with the T-cell hybridomas in the presence of antigen presenting cells and with or without antigen in FCS-containing medium. After 18 hours of incubation at 37° C., an aliquot of culture supernatant (100 μl) was removed and assayed for IL-2 using HT-2 cells as described.

One hybrid that reacted strongly out of 180 screened was identified as RF36.84. The antigen reactivity of RF36.84 compared to that of the VOA-specific RF33.70 hybrdoma is compared in Table 1 below. Data represent the arithmetic mean of cpm of [$^3$H] thymidine incorporated into HT-2 cells. RF36.84 is an anti-influenze+D$^b$ specific T-cell-T-cell hybrid. RF33.70 is an anti-OVA+K$^b$ specific T-cell-T-cell hybrid. Where indicated, NP365-380 (5 μg/ml) or CNBr-cleaved OVA (10 μg/ml) was added to the cultures with RF36.84 and RF33.70, respectively. Splenocytes (5×10$^5$ Exp. 1) or the indicated cell lines (5×10$^4$ Exp. 2) were added as a source of antigen presenting cells (APC). The allelic forms of the K, I, and D MHC molecules that are expressed on the APC's are indicated. R1.1 (CS8/J, H-2$^k$ thymic lymphoma) and DIR cells (D$^b$-transfected R1.1 cells) were kindly provided by Gerald Waneck (Massachusetts General Hospital, Boston, Me.).

TABLE III

Specificity of an anti-influenza T-cell hybridoma

| Exp. | Hybrid | Ag | APC | K | I | D | cpm × 10$^{-3}$ |
|---|---|---|---|---|---|---|---|
| 1 | RF36.84 | − | C57BL/6 | b | b | b | 0.4 |
| | | + | C57BL/6 | b | b | b | 150.6 |
| | | − | B10.A3R | b | b/k | d | 0.4 |
| | | + | B10.A3R | b | b/k | d | 0.5 |
| | | − | B10.A3R | k | k/b | b | 0.7 |
| | | + | B10.A4R | k | k/b | b | 122.6 |
| 1 | RF33.70 | − | C57BL/6 | b | b | b | 0.4 |
| | | + | C57BL/6 | b | b | b | 49.3 |
| | | − | B10.A3R | b | b/k | d | 0.3 |
| | | + | B10.A3R | b | b/k | d | 27.0 |
| | | − | B10.A4R | k | k/b | b | 0.6 |
| | | + | B10.A4R | k | k/b | b | 0.7 |
| 2 | RF36.84 | − | EL4 | b | — | b | 1.5 |
| | | + | EL4 | b | — | b | 142.7 |
| | | − | R1.1 | k | — | k | 1.2 |
| | | + | R1.1 | k | — | k | 1.4 |
| | | − | D$^b$-R1.1 | k | — | k/b | 0.6 |
| | | + | D$^b$-R1.1 | k | — | k/b | 94.5 |

As illustrated in Table 1, the RF36.4 T-cell hybridoma produces IL-2 when stimulated with NP365-380 and EL4 cells in fetal calf serum (FCS)-containing medium. N response is detected when this cell is stimulated with Ag or the APC alone. To determine the MHC specificity of this hybrid, APCs from MHC recombinant inbred mice were used. RF36.84 is stimulated by NP365-380 in the presence of APCs of B10.A4R but not B10.A3R origin. The reciprocal pattern of presentation of Ag is seen when these PACs are tested with the OVA-specific, K$^b$-restricted T-cell-T-cell hybrid RF33.70. This latter control demonstrates that the B10.A3R APCs are active in this experiment. These results demonstrate that the recognition of peptide by RF36.84 is MHC restricted and maps the relevant MHC molecule to the telomeric region of the MHC. To precisely identify the relevant class I molecule, the ability of R1.1 cells (H-2$^k$) that wee transfected with the D$^b$ gene to present peptide to RF36.84 was tested. As shown in Table 1, RF36.84 is stimulated by peptide and the D$^b$-expressing APC but not the control APC. These results confirm that RF36.84 recognizes NP365-380 in association with D$^b$ molecules.

From the above description, it is apparent that the objects of the present invention have been achieved. While only certain illustrative embodiments have been set forth, alternative embodiments will be apparent from the above description to those skilled in the art.

Having described the invention, what is claimed is:

1. An alloreactive, lymphokine-producing, MHC class 1-restricted T-T hybrid comprising the fusion product of:
   (1) BW5147 cells transformed or transfected with a CD8 gene, said cell expressing the CD8 gene product, and
   (2) alloreative T lymphocytes,
   wherein the T-T hybrid expresses the CD8 gene product and exhibits the ability to produce lymphokines in response to antigenic stimulation with target cells bearing allogeneic class I molecules shared by lymphocytes against which the alloreactive lymphocytes were developed but not in response to antigenic stimulation with allogeneic cells bearing only class II molecules.

2. A T-T hybrid according to claim 1, wherein the lymphokine is IL-2.

3. An alloreactive, class I MHC-restricted hybrid according to claim 1, wherein the CD8 gene is murine CD8.

4. An alloreactive, class I MHC-restricted hybrid according to claim 3, wherein the CD8 gene encodes for Lyt-2.2.

5. An alloreactive, class I, MHC-restricted T-T hybrid according to claim 4 identified by ATCC accession number HB10385.

6. An antigen-specific, lymphokine-producing, MHC class I-restricted T-T hybrid comprising the fusion product of:
   (1) BW5147 cells transformed or transfected with a CD8 gene, said cell expressing the CD8 gene product, and
   (2) antigen-specific T lymphocytes obtained from a host,
wherein the T-T hybrid expresses the CD8 gene product and exhibits the ability to produce lymphokines in response to antigenic stimulation with antigen in association with antigen presenting cells which share class I molecules with the host from which the antigen-specific T lymphocytes were derived.

7. A T-T hybrid according to claim 6, wherein the lymphokine is IL-2.

8. A functional, antigen-specific class I MHC-restricted hybrid according to claim 6 wherein the CD8 gene is murine CD8.

9. A functional, antigen-specific class I MHC-restricted T-T hybrid according to claim 8, wherein the CD8 gene encodes for Lyt-2.2.

10. A functional, antigen-specific class I MHC-restricted T-T hybrid according to claim 9, wherein said antigen-specific T lymphocytes are specific for OVA peptide in association with class I $H-2K^b$ antigen presenting cells.

11. A functional, antigen-specific class I, MHC-restricted T-T hybrid according to claim 10 identified by ATCC accession number HB10386.

12. An MHC Class I-restricted T-T hybridoma comprising the fusion product of a BW5147 cell and an activated T cell, wherein the hybridoma expresses the gene product of an exogenous CD8 gene and secretes the lymphokine IL-2 in response to antigenic stimulation with antigen in association with an appropriate class I MHC molecule.

13. A T-T hybridoma according to claim 12 that is alloreactive.

14. A T-T hybridoma according to claim 12 that is antigen-specific.

* * * * *